US012575788B2

(12) United States Patent
Rao et al.

(10) Patent No.: US 12,575,788 B2
(45) Date of Patent: \*Mar. 17, 2026

(54) SYSTEMS, METHODS, APPARATUSES, AND DEVICES FOR FACILITATING TREATMENT FOR ANORECTAL AND PELVIC FLOOR DISORDERS OF USERS USING BIOFEEDBACK THERAPY

(71) Applicant: Neurogut Inc, Naperville, IL (US)

(72) Inventors: Satish Sanku Rao, Hendersonville, NC (US); Amalesh C Sanku, Naperville, IL (US)

(73) Assignee: Neurogut Inc, Naperville, IL (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/996,795

(22) PCT Filed: Dec. 19, 2022

(86) PCT No.: PCT/US2022/053347
§ 371 (c)(1),
(2) Date: Jan. 17, 2025

(87) PCT Pub. No.: WO2024/025592
PCT Pub. Date: Feb. 1, 2024

(65) Prior Publication Data
US 2025/0255548 A1 Aug. 14, 2025

Related U.S. Application Data

(60) Provisional application No. 63/369,780, filed on Jul. 29, 2022.

(51) Int. Cl.
*A61M 25/10* (2013.01)
*A61B 5/00* (2006.01)
(Continued)

(52) U.S. Cl.
CPC .............. *A61B 5/486* (2013.01); *A61B 5/036* (2013.01); *A61B 5/6853* (2013.01); *G16H 15/00* (2018.01);
(Continued)

(58) Field of Classification Search
USPC ........................................................ 600/593
See application file for complete search history.

(56) References Cited

U.S. PATENT DOCUMENTS 7,079,882 B1 7/2006 Schmidt
8,758,387 B2 6/2014 Rao et al.
(Continued)

FOREIGN PATENT DOCUMENTS

FR 2673524 B1 2/1999
KR 100727783 B1 6/2007
(Continued)

OTHER PUBLICATIONS

Rao SS, Rattanakovit K, Patcharatrakul T. Diagnosis and management of chronic constipation in adults. Nat Rev Gastroenterol Hepatol 2016;13:295-305.
(Continued)

*Primary Examiner* — Aurelie H Tu

(57) ABSTRACT

Disclosed herein is a device for facilitating treatment for anorectal and pelvic floor disorders of users using biofeedback therapy. Accordingly, the device may include a body extending between a top end and a bottom end. Further, the device may include a balloon mounted on the top end portion of the body. Further, the device may include a plurality of sensors comprising at least one first sensor, at least one second sensor, and at least one third sensor. Further, the device may include a processing device communicatively coupled with the plurality of sensors. Further, the processing device may be configured for analyzing final
(Continued)

first balloon data, first sensor data, second sensor data, and third sensor data, determining an anorectal anatomical change, and generating a dynamic visual representation and a static visual representation. Further, the device may include a communication device configured for transmitting the dynamic visual representation to an output device.

9 Claims, 13 Drawing Sheets

(51) Int. Cl.
    *A61B 5/03*           (2006.01)
    *G16H 15/00*        (2018.01)
    *G16H 40/67*        (2018.01)

(52) U.S. Cl.
    CPC .......... *G16H 40/67* (2018.01); *A61B 2505/09* (2013.01); *A61M 25/1011* (2013.01)

(56) References Cited

U.S. PATENT DOCUMENTS

| | | | |
|---|---|---|---|
| 9,993,688 B2 | 6/2018 | Siegel | |
| 11,324,999 B2 | 5/2022 | Siegel | |
| 2006/0095032 A1* | 5/2006 | Jackson | A61M 25/10184 606/41 |
| 2009/0024001 A1 | 1/2009 | Parks et al. | |
| 2010/0048520 A1* | 2/2010 | Safdi | A61P 1/04 514/279 |
| 2011/0245703 A1* | 10/2011 | Corn | A61B 5/0205 600/529 |
| 2013/0018308 A1* | 1/2013 | Rao | A63B 71/0622 604/99.04 |
| 2017/0128012 A1 | 5/2017 | Parks et al. | |
| 2017/0332958 A1 | 11/2017 | Gregersen et al. | |
| 2019/0298268 A1* | 10/2019 | Kassab | A61B 5/01 |

FOREIGN PATENT DOCUMENTS

| | | |
|---|---|---|
| RU | 2740730 C2 | 1/2021 |
| WO | 2022040292 A1 | 2/2022 |

OTHER PUBLICATIONS

Menees SB, Almario CV, Spiegel BMR, et al. Prevalence of and Factors Associated With Fecal Incontinence: Results From a Population-Based Survey. Gastroenterology 2018;154:1672-1681 e.

Aoki, Y., Brown, H. W., Brubaker, L., Cornu, J. N., Daly, J. O., & Cartwright, R. Urinary incontinence in women. Nature reviews. Disease primers 2017; 3, 17042. https://doi.org/10.1038/nrdp.2017. 42.

Rao S, Camilleri M. 'Clinical approach to constipation'. In Yamada's Text Book of Gastroenterology, Edited by Podolsky D et al., Chapter 42. (2016): 757-780.

Curtin B, Jimenez E, Rao SSC. Clinical Evaluation of a Patient With Symptoms of Colonic or Anorectal Motility Disorders. J Neurogastroenterol Motil 2020;26:423-436.

Rao SS, Benninga MA, Bharucha AE, et al. ANMS-ESNM position paper and consensus guidelines on biofeedback therapy for anorectal disorders. Neurogastroenterol Motil 2015;27:594-609.

Rao SSC, Valestin JA, Xiang X, et al. Home-based versus office-based biofeedback therapy for constipation with dyssynergic defecation: a randomised controlled trial. Lancet Gastroenterol Hepatol 2018;3:768-777.

Rao SS, Seaton K, Miller M, et al. Randomized controlled trial of biofeedback, sham feedback, and standard therapy for dyssynergic defecation. Clin Gastroenterol Hepatol 2007;5:331-8.

Firinci S, Yildiz N, Alkan H, Aybek Z. Which combination is most effective in women with idiopathic overactive bladder, including bladder training, biofeedback, and electrical stimulation? A prospective randomized controlled trial. Neurourol Urodyn. 2020;39(8):2498-508.

Rao SSC, Go JT, Valestin J, et al. Home Biofeedback for the Treatment of Dyssynergic Defecation: Does It Improve Quality of Life and Is It Cost-Effective? Am J Gastroenterol 2019;114:938-944.

Rao SS, Bharucha AE, Chiarioni G, et al. Anorectal Disorders. Gastroenterology 2016;150:1430-1442.

Jiang AC, Panara A, Yan Y, et al. Assessing Anorectal Function in Constipation and Fecal Incontinence. Gastroenterol Clin North Am 2020;49:589-606.Yan Y, Xiang X, Sharma A, et al. Validation of a prospective stool diary instrument for assessment of fecal incontinence. Gastroenterology 2019;156:S-355.

Rao SS, Coss-Adame E, Tantiphlachiva K, et al. Translumbar and transsacral magnetic neurostimulation for the assessment of neuropathy in fecal incontinence. Dis Colon Rectum 2014;57:645-52.

Yan Y, Jimenez E, Sharma A, et al. How useful is constipation stool app compared to paper stool dairy-randomized study of constipation and healthy subjects. Gastroenterology 2020; 158:S400.

Jimenez E, Yan Y, Sharma A, Parr R, Herekar A, Eubanks A, Karunaratne T, Sanku A, Rao SSC. Fecal Incontinence (FI) Stool APP is a Reliable and Valid Instrument for Leakage Assessment: RCT in FI and Healthy Subjects. J Gastroenterol & Hepatol 2019;34:457-457. Sa1681.

Rao SS. Endpoints for therapeutic interventions in fecal incontinence: small step or game changer. Neurogastroenterol Motil 2016;28:1123-33.

Patcharatrakul T, Pitisuttithum P, Rao S, et al. 'Biofeedback therapy'. In: Rao SS, Lee YY, Ghoshal UC, ed. Clinical and basic neurogastroenterology and motility. 1st Ed. Cambridge, MA, USA, Academic Press 2020; 517-532.

Whitehead W, Rao SSC, Lowry A, Nagle D, Varma M, Bitar K, Bharucha A, Hamilton F. Treatment of Fecal Incontinence: State-of-the-Science Summary for the National Institute of Diabetes and Digestive and Kidney Disease Workshop. Am J Gastroenterol. 2015; 110(1):138-46. Epub Oct. 21, 2014. PMID: 25331348.

Haddix AC, Teutsch SM, Corso PS, editors. Prevention effectiveness: a guide to decision analysis and economic evaluation. Oxford University Press; 2003.

Xiang X, Sharma A, Patcharatrakul T, Yan Y, Karunaratne T, Parr R, Ayyala DN, Hall P, Rao SS. Randomized controlled trial of home biofeedback therapy versus office biofeedback therapy for fecal incontinence. Neurogastroenterology & Motility. Nov. 2021;33(11):e14168.

\* cited by examiner

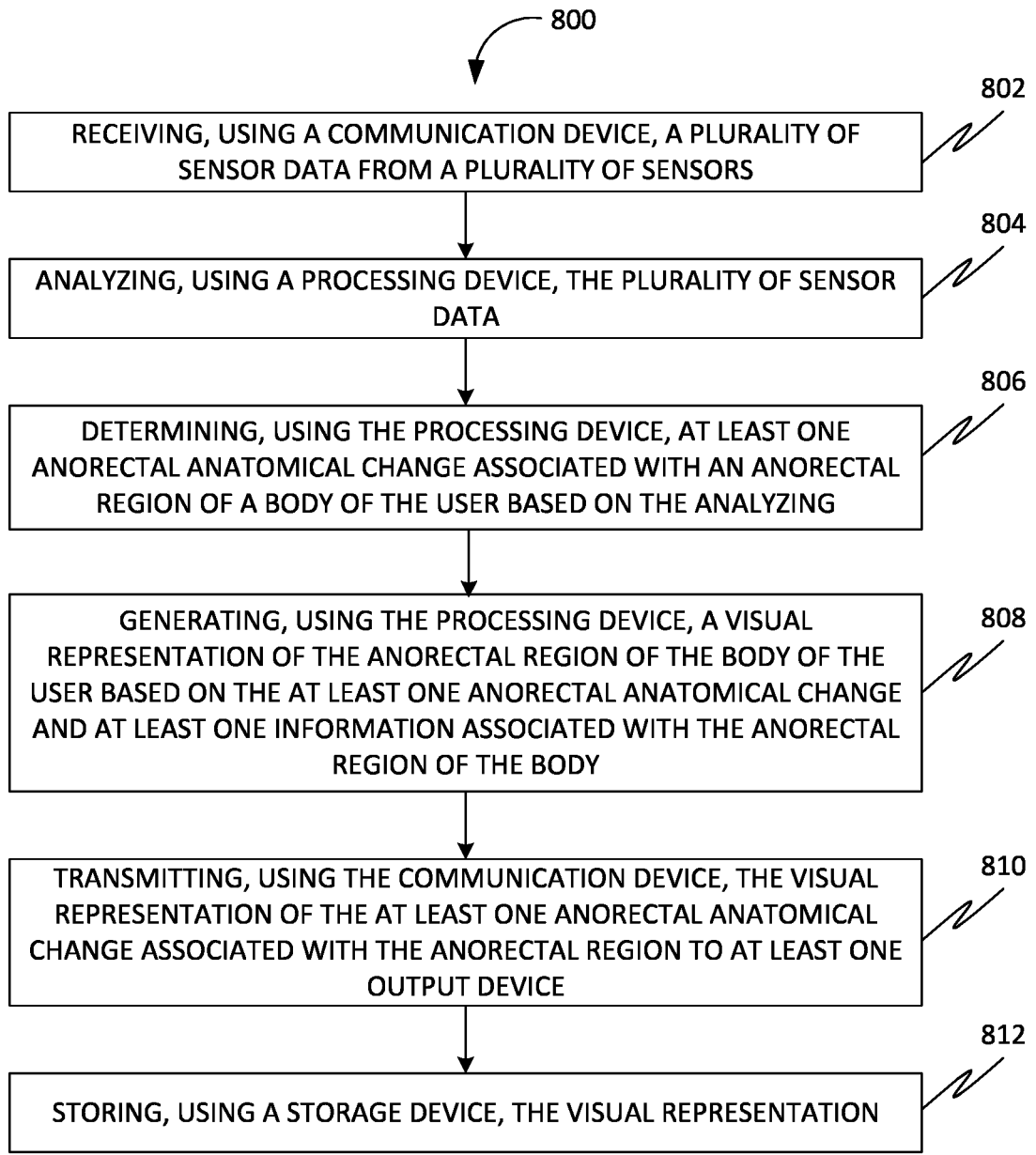

800

802
RECEIVING, USING A COMMUNICATION DEVICE, A PLURALITY OF SENSOR DATA FROM A PLURALITY OF SENSORS

804
ANALYZING, USING A PROCESSING DEVICE, THE PLURALITY OF SENSOR DATA

806
DETERMINING, USING THE PROCESSING DEVICE, AT LEAST ONE ANORECTAL ANATOMICAL CHANGE ASSOCIATED WITH AN ANORECTAL REGION OF A BODY OF THE USER BASED ON THE ANALYZING

808
GENERATING, USING THE PROCESSING DEVICE, A VISUAL REPRESENTATION OF THE ANORECTAL REGION OF THE BODY OF THE USER BASED ON THE AT LEAST ONE ANORECTAL ANATOMICAL CHANGE AND AT LEAST ONE INFORMATION ASSOCIATED WITH THE ANORECTAL REGION OF THE BODY

810
TRANSMITTING, USING THE COMMUNICATION DEVICE, THE VISUAL REPRESENTATION OF THE AT LEAST ONE ANORECTAL ANATOMICAL CHANGE ASSOCIATED WITH THE ANORECTAL REGION TO AT LEAST ONE OUTPUT DEVICE

812
STORING, USING A STORAGE DEVICE, THE VISUAL REPRESENTATION

SYSTEMS, METHODS, APPARATUSES, AND DEVICES FOR FACILITATING TREATMENT FOR ANORECTAL AND PELVIC FLOOR DISORDERS OF USERS USING BIOFEEDBACK THERAPY

The current application is a 371 of international Patent Cooperation Treaty (PCT) application PCT/US2022/053347 filed on Dec. 19, 2022. The PCT application PCT/US2022/053347 claims a priority to the U.S. provisional patent application Ser. No. 63/369,780 filed on Jul. 29, 2022.

FIELD OF THE INVENTION

Generally, the present disclosure relates to the field of medical and laboratory equipment. More specifically, the present disclosure relates to systems, methods, apparatuses, and devices for facilitating treatment for anorectal and pelvic floor disorders of users using biofeedback therapy.

BACKGROUND OF THE INVENTION

Dyssynergic defecation (DD), fecal incontinence (FI), and urinary incontinence (UI) are common anorectal and pelvic floor disorders that affect 25% of the population. Dyssynergic defecation is a behavioral problem characterized by incoordination of the anal and rectal muscles during defecation. Fecal and urinary incontinence is caused by damage to anorectal muscles and nerves as well as rectal and bladder sensation and holding capacity. Treatment options are limited for these conditions, and over 50% of patients are dissatisfied with current treatment modalities. Commonly used therapies for DD include laxatives that often fail. Likewise, FI and UI are treated with antidiarrheal drugs (loperamide), anticholinergic drugs (Detrol) or surgical repair of torn anal sphincter muscles, or injection of sphincter bulking agents (NASHA dx) to create a protective barrier. Each of these treatments only addresses one or more mechanisms of these multifactorial disorders and are therefore only partially effective (10-30% of patients), and often have significant side effects that limit their wider use.

Biofeedback therapy is a durable, efficacious, safe, mechanistically based, non-invasive, and low-risk treatment that remedies the multifactorial dysfunctions that cause dyssynergic defecation, FI, and UI. Biofeedback therapy has been proven to be efficacious and safe in large randomized controlled trials. In a recent trial, it was shown that home biofeedback therapy was both efficacious, safe, and cost-effective for the treatment of DD and significantly improved quality of life (7 and 10). Large randomized trials have also shown that biofeedback therapy is efficacious and safe in FI and UI and a recent trial showed that home biofeedback is as efficacious as office biofeedback for FI (20). There is no standardized method or device for the treatment of DD hampering health care providers' ability to provide biofeedback therapy. Most systems are adaptations of anorectal manometry or urodynamic systems. These systems are commonly used for performing diagnostic studies and are designed for use by medical personnel. For example, the monitor display for anorectal manometry is designed for scientific measurements of pressure or electromyographic changes and not for lay persons to understand the abnormalities in pelvic floor function that are causing their problem(s) or learn how to correct them.

Consequently, current methods used for providing biofeedback therapy are cumbersome, have not been purposefully designed, and are not user-friendly. Also, there is no home biofeedback therapy system for DD. Finally, there is no comprehensive system for performing both home and office biofeedback therapy for DD, FI, or UI.

Therefore, there is a large unmet need for improved systems, methods, apparatuses, and devices for performing biofeedback treatment of anorectal and pelvic floor disorders that may overcome one or more of the aforementioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a device for facilitating treatment for anorectal and pelvic floor disorders of users using biofeedback therapy, in accordance with some embodiments. Accordingly, the device may include a body extending between a top end and a bottom end. Further, the body may include a top end portion, a middle portion, and a bottom end portion. Further, the body may be configured to be placed in a rectum of a user by inserting the body into the rectum. Further, the top end portion may be positioned adjacent to a first region of the rectum, the middle portion may be positioned adjacent to a second region of the rectum, and the bottom end portion may be positioned adjacent to a third region of the rectum based on the placing of the body in the rectum. Further, the device may include a balloon mounted on the top end portion of the body. Further, the device may include a plurality of sensors may include at least one first sensor, at least one second sensor, and at least one third sensor. Further, the at least one first sensor may be configured for generating at least one final first balloon data based on detecting at least one balloon characteristic associated with the balloon after the placing of the body in the rectum. Further, the at least one balloon characteristic corresponds to at least one maneuver performed by the user. Further, the at least first sensor may be configured for generating at least one first sensor data based on detecting at least one region characteristic associated with the first region. Further, the at least one second sensor may be configured for generating at least one second sensor data based on detecting the at least one region characteristic associated with the second region. Further, the at least one third sensor may be configured for generating at least one third sensor data based on detecting the at least one region characteristic associated with the second third region. Further, the device may include a processing device communicatively coupled with the plurality of sensors. Further, the processing device may be configured for analyzing the at least one final first balloon data, the at least one first sensor data, the at least one second sensor data, and the at least one third sensor data. Further, the processing device may be configured for determining at least one anorectal anatomical change associated with the rectum based on the analyzing. Further, the processing device may be configured for generating at least one dynamic visual representation of a human anatomy for stimulating the at least one anorectal anatomical change during the at least one maneuver in real-time based on the at least one anorectal anatomical change and a static visual representation of the human anatomy. Further, the device may include a communication device communicatively coupled with the processing device. Further, the communication device may be configured for transmitting the at least one dynamic visual representation to at least one output device.

Further disclosed herein is a device for facilitating treatment for anorectal and pelvic floor disorders of users using biofeedback therapy, in accordance with some embodiments. Accordingly, the device may include a body extending between a top end and a bottom end. Further, the body may include a top end portion, a middle portion, and a bottom end portion. Further, the body may be configured to be placed in a rectum of a user by inserting the body into the rectum. Further, the top end portion may be positioned adjacent to a first region of the rectum, the middle portion may be positioned adjacent to a second region of the rectum, and the bottom end portion may be positioned adjacent to a third region of the rectum based on the placing of the body in the rectum. Further, the device may include a base attached to the bottom end. Further, the base may be not placed inside the rectum. Further, the base facilitates the inserting of the body in the rectum. Further, the device may include a balloon mounted on the top end portion of the body. Further, the device may include a plurality of sensors may include at least one first sensor, at least one second sensor, and at least one third sensor. Further, the at least one first sensor may be configured for generating at least one final first balloon data based on detecting at least one balloon characteristic associated with the balloon after the placing of the body in the rectum. Further, the at least one balloon characteristic corresponds to at least one maneuver performed by the user. Further, the at least one first sensor may be configured for generating at least one first sensor data based on detecting at least one region characteristic associated with the first region. Further, the at least one second sensor may be configured for generating at least one second sensor data based on detecting the at least one region characteristic associated with the second region. Further, the at least one third sensor may be configured for generating at least one third sensor data based on detecting the at least one region characteristic associated with the second third region. Further, the device may include a processing device communicatively coupled with the plurality of sensors. Further, the processing device may be configured for analyzing the at least one final first balloon data, the at least one first sensor data, the at least one second sensor data, and the at least one third sensor data. Further, the processing device may be configured for determining at least one anorectal anatomical change associated with the rectum based on the analyzing. Further, the processing device may be configured for generating at least one dynamic visual representation of a human anatomy for stimulating the at least one anorectal anatomical change during the at least one maneuver in real-time based on the at least one anorectal anatomical change and a static visual representation of the human anatomy. Further, the device may include a communication device communicatively coupled with the processing device. Further, the communication device may be configured for transmitting the at least one dynamic visual representation to at least one output device.

Further disclosed herein is a device for facilitating treatment for anorectal and pelvic floor disorders of users using biofeedback therapy, in accordance with some embodiments. Accordingly, the device may include a body extending between a top end and a bottom end. Further, the body may include a top end portion, a middle portion, and a bottom end portion. Further, the body may be configured to be placed in a rectum of a user by inserting the body into the rectum. Further, the top end portion may be positioned adjacent to a first region of the rectum, the middle portion may be positioned adjacent to a second region of the rectum, and the bottom end portion may be positioned adjacent to a third region of the rectum based on the placing of the body in the rectum. Further, the device may include a balloon mounted on the top end portion of the body. Further, the device may include a plurality of sensors may include at least one first sensor, at least one second sensor, and at least one third sensor. Further, the at least one first sensor may be configured for generating at least one final first balloon data based on detecting at least one balloon characteristic associated with the balloon after the placing of the body in the rectum. Further, the at least one balloon characteristic corresponds to at least one maneuver performed by the user. Further, the at least one first sensor may be configured for generating at least one first sensor data based on detecting at least one region characteristic associated with the first region. Further, the at least one second sensor may be configured for generating at least one second sensor data based on detecting the at least one region characteristic associated with the second region. Further, the at least one third sensor may be configured for generating at least one third sensor data based on detecting the at least one region characteristic associated with the second third region. Further, the device may include a processing device communicatively coupled with the plurality of sensors. Further, the processing device may be configured for analyzing the at least one final first balloon data, the at least one first sensor data, the at least one second sensor data, and the at least one third sensor data. Further, the processing device may be configured for determining at least one anorectal anatomical change associated with the rectum based on the analyzing. Further, the processing device may be configured for generating at least one dynamic visual representation of a human anatomy for stimulating the at least one anorectal anatomical change during the at least one maneuver in real-time based on the at least one anorectal anatomical change and a static visual representation of the human anatomy. Further, the device may include a communication device communicatively coupled with the processing device. Further, the communication device may be configured for transmitting the at least one dynamic visual representation to at least one output device. Further, the communication device may be configured for receiving an indication associated with the user and one of a plurality of anorectal and pelvic floor disorders from at least one input device. Further, the communication device may be configured for transmitting at least one instruction to the at least one output device. Further, the device may include a storage device communicatively coupled with the communication device. Further, the storage device may be configured for retrieving at least one treatment program associated with the user for one of the plurality of anorectal and pelvic floor disorders. Further, the processing device may be communicatively coupled with the storage device. Further, the processing device may be configured for generating the at least one instruction for at least one therapy session based on the at least one treatment program. Further, the at least one instruction instructs the user for performing the at least one maneuver after the placing of the body in the rectum.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

FIG. 8 is a flowchart of a method 800 for performing biofeedback treatment of anorectal and pelvic floor disorders, in accordance with some embodiments.

DETAIL DESCRIPTIONS OF THE INVENTION

Figure 1:
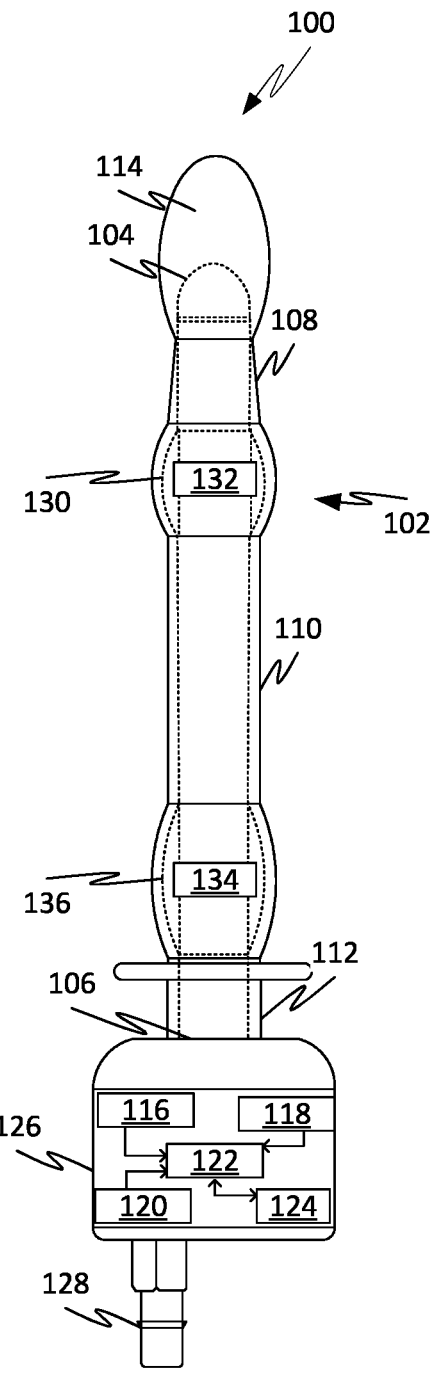
FIG. 1 is a front view of a device 100 for facilitating treatment for anorectal and pelvic floor disorders of users using biofeedback therapy, in accordance with some embodiments.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of systems, methods, apparatuses, and devices for facilitating treatment for anorectal and pelvic floor disorders of users using biofeedback therapy, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g., a mail server, a web server, a real-time communication server, an FTP server, a virtual server, a proxy server, a DNS server, etc.), a quantum computer, and so on. Further, one or more client devices and/or the server computer may be configured for executing a software application such as, for example, but not limited to, an operating system (e.g., Windows, Mac OS, Unix, Linux, Android, etc.) in order to provide a user interface (e.g., GUI, touch-screen based interface, voice-based interface, gesture-based interface, etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, public database, a private database and so on. Further, the communication device may be configured for communicating with the one or more external devices over one or more communication channels. Further, the one or more communication channels may include a wireless communication channel and/or a wired communication channel.

Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g., username, password, passphrase, PIN, secret question, secret answer, etc.) and/or possession of a machine readable secret data (e.g., encryption key, decryption key, bar codes, etc.) and/or or possession of one or more embodied characteristics unique to the user (e.g., biometric variables such as, but not limited to, fingerprint, palm-print, voice characteristics, behavioral characteristics, facial features, iris pattern, heart rate variability, evoked potentials, brain waves, and so on) and/or possession of a unique device (e.g., a device with a unique physical and/or chemical and/or biological characteristic, a hardware device with a unique serial number, a network device with a unique IP/MAC address, a telephone with a unique phone number, a smartcard with an authentication token stored thereupon, etc.). Accordingly, the one or more steps of the method may include communicating (e.g., transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g., the server computer, a client device, etc.) corresponding to the performance of the one or more steps, physical state and/or physiological state and/or psychological state of the user, physical state (e.g., motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g., a real-time clock), a location sensor (e.g., a GPS receiver, a GLONASS receiver, an indoor location sensor, etc.), a biometric sensor (e.g., a fingerprint sensor), and a device state sensor (e.g., a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g., initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview

The present disclosure describes systems, methods, apparatuses, and devices for facilitating treatment for anorectal and pelvic floor disorders of users using biofeedback therapy.

Further, the present disclosure describes dyssynergic defecation and incontinence training devices and methods for home and office biofeedback therapy.

Further, the present disclosure generally relates to systems and methods for non-invasive biofeedback treatments of anorectal and pelvic floor disorders. More specifically, the present disclosure describes a novel, integrated, comprehensive method and device system including probe, inflatable balloon, software, voice-guided instructions, and mobile phone or monitor display systems for performing home and/or office biofeedback therapy for dyssynergic defecation, fecal incontinence, and urinary incontinence.

Further, the present disclosure describes a probe, a smartphone application (App), and biofeedback software, and a harness system. Further, the probe may be a 3-sensor pressure anorectal probe with a balloon for placement in the rectum for assessment of anal and rectal pressures. Further, the balloon may be an air bag. The probe has a hub at the base that has three external strain gauge pressure transducers, ports for balloon inflation and a microprocessor, and a battery. The probe is designed to communicate wirelessly with the smartphone app. Further, an external strain gauge pressure transducer of the three external strain gauge pressure transducers may include a sensor. Further, the microprocessor may be a processing device.

Further, the smartphone app may be used to display real-time animations and pictorial displays of anorectal anatomical changes rather than the traditional LCD lights and computer monitors. This immensely improves the ability to provide biofeedback training. Also, the interactive images of the human anatomy that are both dynamic and change in real-time during the biofeedback maneuvers can prove to be a significant advance over line tracings showing pressure or EMG changes that many patients find difficult to comprehend. These animated real-time images could enable the patient to visualize and directly connect with their anal, rectal, or pelvic floor muscle dysfunction or rectal sensory dysfunction that is causing their bowel or urinary problem. Also, the use of Bluetooth technology will enable wireless transmission of the pressure changes from inside the body to a smartphone display system, avoiding the hassles of long wires connecting a probe with a hand-held device, to view pressure changes in the anus and rectum for biofeedback purposes. Further, the ability to provide voice guided instructions and written instructions displayed on the screen using the smartphone APP will provide a structured and standardized treatment program on how to perform biofeedback training at home that mirrors the office biofeedback training. This new home biofeedback system could significantly improve the current method of performing biofeedback training.

Further, the biofeedback software is a unique exclusively configured software that is designed to work in conjunction with the bioanatoner (probe) in a physician's office/hospital setting. This software will provide a secure connection between the 3-channel bioanatoner probe using Bluetooth and a web-based data collector and report generator to a desktop computer. This web-based application will be used by health care providers and biofeedback therapists to perform Biofeedback therapy for Dyssynergic Defecation, Fecal Incontinence, and Urinary Incontinence in an office or Hospital Setting. This user-friendly APP will allow Data Collection, Report Generation, and biofeedback data analysis for assessing the progress of biofeedback therapy with each patient. The secure web interface also serves as a backup resource for all recordings made by bioanatoner system during each biofeedback therapy session and allows for charting and monitoring changes and comparison with previous training sessions. Also, the APP generates a graphical summary of the training, providing immediate feedback to the user regarding their performance, and facilitate remote monitoring by health care providers for interacting with patients and providing them with encouragement or tips for improvement.

Further, the present disclosure describes a study on constipation with dyssynergic defecation. Further, constipation with dyssynergic defecation affects up to 20 million Americans (1). Likewise, fecal incontinence (FI) affects 1 in 7 Americans (2). Also, 28 million Americans have urinary incontinence (UI) whose care alone costs $15 billion dollars a year (3). Thus, all three problems significantly affect the quality of life and cause psychosocial distress and consume significant healthcare resources (1-5). FI patients have approximately 55% more overall healthcare expenditure than their continent peers (20). In a study of 76,854 patients enrolled in a medical program in California, the total healthcare expenditure for patients with constipation over a 15-month period was $18,891,008, with an average cost of $246 per patient (4). Thus, these 3 pelvic floor problems impose a significant healthcare burden, especially on women and the elderly, and carry a significant impact on society.

Biofeedback therapy has been shown to be effective in improving dyssynergic defecation in 70% of patients (1, 4, 5, and 7-9) and in up to 65% of patients with FI (20 and 7). Likewise, 51-70% of patients with urinary incontinence report improvement in urinary leakage (3 and 10). Biofeedback has also been shown to be superior to Kegel exercises in patients with both FI and UI (3, 7, and 10). Thus, this treatment remains the mainstay for nearly 3 decades. However, the standard method of administering biofeedback therapy uses an office-based, outpatient treatment protocol that consists of placing a probe in the rectum, which is connected to a pressure/EMG recorder, and a monitor for displaying the pressure changes (7 and 10). This system facilitates visual and verbal feedback to the patient and the therapist. However, office-biofeedback therapy is not widely available, is labor intensive for patients and therapists, must be supervised by skilled personnel, and requires multiple office visits, on average between 6-10 visits/year (20, 7, and 8). It is therefore imperative that a more pragmatic biofeedback treatment program that can be administered at home ought to be developed (20 and 8).

Previous studies have shown that home biofeedback training can be just as useful as office-based training, both for constipation with dyssynergia and fecal incontinence (20 and 8). A recent study showed that the total median cost per patient was significantly lower for home biofeedback ($1,112.00) than office biofeedback ($1,943.00) resulting in a cost saving of $830.00, and an incremental cost-effectiveness ratio of $20,752.75 in favor of home biofeedback (11). These studies were also performed with older technology that included the placement of anal probes connected to hand-held monitors with a liquid crystal display of flashing lights indicating changes in anal pressures (20 and 8). However, these methods are cumbersome and not user-friendly and do not provide realistic feedback to the patient regarding the underlying dysfunctions. Further, there is no commercially available home biofeedback system for dyssynergic defecation.

The advent of newer digital technology using smartphone app-based applications, with real-time animations and pictorial displays of anorectal anatomical changes than the traditional LCD lights and computer monitors, if adopted, could immensely improve the ability to provide biofeedback training. To obtain the intraluminal pressure signals, a 3-sensor anorectal probe with a balloon will be placed in the rectum for the assessment of anal and rectal pressures, and this probe will be designed to communicate wirelessly with the smartphone app using Bluetooth technology. Also, the interactive images of the human anatomy that are both dynamic and change in real-time during the biofeedback maneuvers can prove to be a significant advance over line tracings showing pressure or EMG changes that many patients find difficult to comprehend. These animated real-time images could enable the patient to visualize and directly connect with their anal, rectal, or pelvic floor muscle dysfunction that is causing their bowel or urinary problem. The use of Bluetooth technology will avoid the hassles of connecting a probe with a hand-held device, to view pressure changes. Further, the ability to provide voice guided instructions using the smartphone APP will provide a structured treatment program on how to perform biofeedback training at home, using a format that mirrors the office biofeedback training. This new home biofeedback system could significantly improve the current method of performing biofeedback training.

Home Biofeedback is not only convenient but could be less costly and cost-effective. However, the cost-effectiveness of home biofeedback therapy for UI and FI has not been systematically evaluated. Importantly, a scientifically tested and user-friendly biofeedback system could not only make this treatment more widely available but also help millions of patients with these three common pelvic floor problems, who do not have access to such a therapeutic option.

Further, the present disclosure describes the office biofeedback app for bioanatoner 3 system. This unique exclusively configured app and software are designed to work in conjunction with the bioanatoner model 3 in a physician's office/hospital setting. This software app will provide a secure connection between the 3-channel bioanatoner probe using Bluetooth and a web-based data collector and report generator to a desktop computer. Research physicians and biofeedback therapists who perform biofeedback therapy for fecal incontinence and urinary incontinence in an office or hospital setting will use this web-based application. This user-friendly app will allow data collection, report generation, and biofeedback data Analysis for assessing the progress of biofeedback therapy with each patient. The secure web interface also serves as a backup resource for all recordings made by bioanatoner system during each biofeedback therapy session and allows for charting and monitoring changes and comparison with previous training sessions.

Further, the present disclosure describes trial one for office-based biofeedback therapy (OB). Further, the Office-based biofeedback therapy (OB) is efficacious for constipation with dyssynergic defecation (DD). However, it requires skilled staff, and multiple visits, and is only available in selected centers. Whether home-based biofeedback therapy (HB) is also effective is not known. In a randomized controlled trial, patients with DD (Rome III) received either OB or HB. OB comprised of therapist-guided six biweekly sessions of pelvic floor training. HB comprised of selftraining at home, 20 minutes, twice a day, after self-inserting a probe attached to a display box that provided individual, performance-specific, visual feedback. Anorectal physiology and daily symptom diary were assessed and compared. Subjects with normalization of dyssynergic defecation and >1 increase in the number of complete spontaneous bowel movements (CSBM)/week at 3 months were considered responders. Cost outcomes were assessed using hospital billing records and questionnaires. ITT non-inferiority analyses and per protocol analyses were performed using the one-sided t-test with a margin (bound) added to the null value. Further, 100 subjects (96 F) participated, 83 completed [Home=38/50, office=45/50]. Thirty-four (68%) patients were responders in HB and 35/50 (70%) in OB. The number of CSBM/week, dyssynergia pattern, balloon expulsion time, digital maneuver use, and bowel satisfaction improved significantly (p<0.0001) from baseline with both treatments. The effect of HB was non-inferior to OB for the primary subjective and physiologic outcomes of a number of CSBM/week, bowel satisfaction, and balloon expulsion time in both ITT and per protocol analyses, and for dyssynergia in the per protocol analysis. The home device was well tolerated. There were no adverse events. HB incurred significantly lower costs than OB (p<0.01), with a saving of $860.00. Further, HB significantly improves bowel symptoms and physiology and is as effective as OB. HB is well tolerated, less costly, and should be the preferred treatment for DD.

Further, the present disclosure describes trial two of biofeedback therapy. Further, biofeedback therapy is useful for the treatment of fecal incontinence (FI) but is not widely available and is labor intensive. Home biofeedback therapy (HBT) is investigated if it is non-inferior to office biofeedback therapy (OBT). Further, Patients with FI (≥1 episode/week) were randomized to HBT or OBT for 6 weeks. HBT was performed daily using a novel device that provided resistance training and electrical stimulation with voice-guided instructions. OBT consisted of six weekly sessions. Both methods involved anal strength, endurance, and coordination training. The primary outcome was a change in weekly FI episodes. FI improvement was assessed with stool diaries, validated instruments (FISI, FISS, and ICIQ-B), and anorectal manometry using intention-to-treat analysis. Further, thirty (F/M=26/4) FI patients (20 in HBT, 10 in OBT) participated. Weekly FI episodes decreased significantly after HBT (Δ±95% confidence interval: 4.7±1.8, compared with baseline, p=0.003) and OBT (3.7±1.6, p=0.0003) and HBT was non-inferior to OBT (p=0.2). The FISI and FISS scores improved significantly in the HBT group (p<0.02). Bowel pattern, bowel control, and quality of life (QOL) domains (ICIQ-B) improved significantly in the HBT arm (p<0.023). Resting and maximum squeeze sphincter pressures significantly improved in both HBT and OBT groups and sustained squeeze pressure in HBT, without group differences. Further, home biofeedback therapy is non-inferior to OBT for FI treatment. Home biofeedback is safe, effective, improves QOL, and through increased access could facilitate improved management of FI.

Further, the present disclosure describes a bioanatoner probe system. Further, the bioanatoner probe system may include a bioanatoner having a dimension of 10 cm×1 cm. Further, the bioanatoner probe system may include three sensors (Anal, Rectal, and Rectal Balloon sensor). Further, the bioanatoner may be comprised of silicone plastic. Further, the bioanatoner may include a core that is semiflexible. Further, the bioanatoner may include a shell that is flexible. Further, the bioanatoner may include a rectal balloon that is inflatable up to 50 cc. of air with an external syringe and has a maximum diameter of 2.5 cm.

Further, the present disclosure describes a bioanatoner probe. Further, the bioanatoner probe may include strain gauge pressure transducers, at least one port for inflation of a balloon, at least one microprocessor, and at least one battery. Further, the bioanatoner probe may be configured to be inserted in an anal and a rectum. Further, the bioanatoner probe may be made up of silicon plastic. Further, the bioanatoner may include at least one core and at least one shell. Further, the at least one core may be semi flexible. Further, the at least one shell may be flexible. Further, the strain gauge pressure transducers may include a plurality of sensors. Further, the plurality of sensors may include at least one anal sensor, at least one rectal sensor, and at least one rectal balloon sensor. Further, a transducer may be a device for converting energy from one form to another form. Further, a strain gauge pressure transducer may be the device to vary an electrical resistance with applied pressure. Further, the at least one port for the inflation of the balloon may be configured to be inflating the balloon by transferring the fluid using the at least one port. Further, the fluid may include air and a liquid. Further, the microprocessor may be configured to be processing data received by at least one sensor based on the change in pressure detected by the plurality of sensors. Further, the at least one battery may be configured to be providing power to the bioanatoner probe. Further, the at least one smartphone app may be configured to be providing real-time pictures and animations of anatomical changes in the rectum. Further, the real-time animations may enable at least one patient to visualize and directly view the anal, rectum, and pelvic floor muscle dysfunctions of the at least one patient. Further, wireless connectivity may be configured to be establishing a connection between the bioanatoner probe and the at least one smartphone app. Further, the wireless connectivity may be configured to be enabling pressure changes from inside the rectum of the at least one patient to at least one smartphone display system. Further, the wireless connectivity may include Bluetooth connectivity, Wi-Fi connectivity, etc. Further, at least one smartphone may be configured to be providing voice-guided instructions using the at least one smartphone app. Further, the voice-guided instructions may be used for a structured treatment at home for the biofeedback therapy at the home. Further, at least one biofeedback software may be configured to be working in conjunction with the bioanatoner probe in a hospital, an office, etc. Further, at least one communication device associated with at least one computing device may be using Bluetooth connectivity for receiving the data from the bioanatoner probe. Further, at least one processing device may be configured for generating a report based on the data received by the at least one computing device. Further, the computing device may include a laptop, a desktop, a tablet, etc. Further, at least one biofeedback software may be configured for collecting the data, perform data analysis and generate the report as well as provide graphic illustrations and comparative performance charts, providing a summary of the biofeedback data analysis for at least one patient.

Further, in some embodiments, dyssynergic defecation may be a condition affecting the coordination of movement of stool through the anorectum and pelvic floor muscle region. Further, the pelvic floor muscle may be fixedly disposed in a lower abdomen. Further, the pelvic floor muscle may be allowing a bowel movement to pass normally. Further, the pelvic floor muscle allows bowel movement by supporting a plurality of organs. Further, the plurality of organs may include the rectum, the anus, the uterus, and the bladder. Further, the dyssynergic defecation may be occurring by non-coordination of the abdominal, rectal, anal, and pelvic floor muscles with one or more surrounding muscles and one or more nerves. Further, the coordination of the one or more surrounding muscles and one or more nerves may be responsible for the normal bowel movement.

Further, in some embodiments, fecal incontinence may be an uncontrollable bowel movement by the at least one patient. Further, fecal incontinence may include uncontrollable bowel movements at an unwanted time. Further, uncontrollable bowel movements may leak out from the rectum. Further, the leak of the uncontrollable bowel movement may be occurring without the knowledge of the patient. Further, fecal incontinence may be occurring more in a female subject. Further, fecal incontinence may be occurring less in a male subject. Further, a symptom of fecal incontinence may include a stool leak during the passage of gas, a stool leak during physical activity, a stool leak with complete loss of bowel control or small amounts, etc. Further, the rectum and anus may be working correctly for a natural bowel movement.

Further, in some embodiments, urinary incontinence may be occurring because of an uncontrollable urinary bladder. Further, the uncontrollable urinary bladder may leak out urine during a cough, a sneeze, a laugh, etc. Further, the leak out of urine may be uncontrollable by at least one patient. Further, urinary incontinence may occur more commonly in older people. Further, urinary incontinence may be less in younger people. Further, urinary incontinence may include stress incontinence, urge incontinence, overflow incontinence, functional incontinence, and mixed incontinence. Further, stress incontinence may be occurring by exerting a first pressure on the urinary bladder by the cough, the sneeze, the laugh, an exercise, etc. Further, the urge incontinence may be an intense urge for urination followed by uncontrollable loss of urine. Further, the urge incontinence may be occurring to an infection, a neurological disorder, diabetes, etc. Further, overflow incontinence may include frequent urination and constant urination. Further, frequent urination and constant urination may be responsible for an incomplete empty urinary bladder. Further, functional incontinence may include a physical impairment and a mental impairment. Further, the physical impairment and the mental impairment may be responsible for keeping the at least one patient away from a toilet. Further, mixed incontinence may include more than one type of urinary incontinence. Further, the mixed incontinence may include a combination of stress incontinence and urge incontinence.

In further embodiments, the disclosed apparatus may include an anorectal probe, a plurality of sensors, a manually inflatable balloon on the anorectal probe, a communication device, a processing device, and at least one battery. Further, the anorectal and pelvic floor disorders may include Dyssynergic defecation (DD), fecal incontinence (FI), and urinary incontinence (UI).

Further, the anorectal probe may extend between a top end and a base end. Further, the anorectal probe may be configured to be placed in a rectum of a user by inserting the top end into the rectum. Further, the user may be a patient. Further, the anorectal probe may include at least one balloon and at least one port fluidly coupled with the at least one balloon. Further, the at least one port may be used for at least one of inflating and deflating the at least one balloon. Further, the anorectal probe may include a hub disposed at the base end of the anorectal probe Further, the plurality of sensors may be disposed on the anorectal probe. Further, the plurality of sensors may include a first sensor, a second sensor, and a third sensor. Further, a balloon of the manually inflatable balloon may be disposed on the anorectal probe close to the first sensor and connected with a manual balloon inflation system. Further, the balloon may communicate with the first sensor. Further, the first sensor may be disposed on the anorectal probe proximal to the top end. Further, the second sensor may be disposed on the anorectal probe between the top end and the base end. Further, the third sensor may be disposed on the anorectal probe proximal to the base end. Further, the first sensor may be configured for generating a first sensor data based on detecting at least one characteristic associated with a first region of the rectum during at least one maneuver performed by the user. Further, the second sensor may be configured for generating a second sensor data based on detecting the at least one characteristic associated with a second region of the rectum during the at least one maneuver performed by the user. Further, the third sensor may be configured for generating a third sensor data based on detecting the at least one characteristic associated with a third region of the rectum during the at least one maneuver performed by the user. Further, the first sensor associated with the balloon may be configured for generating intrarectal balloon distension and/or pressure measurements associated with the balloon. Further, the first sensor associated with the balloon may be configured for generating rectal sensory measurement data based on detecting at least one characteristic associated with the first region of the rectum. Further, the at least one characteristic may include a movement, a pressure, a temperature, a void, a shape, etc. associated with at least one of the first region, the second region, and the third region of the rectum.

Further, the processing device may be disposed on the anorectal probe. Further, the processing device may be communicatively coupled with the plurality of sensors. Further, the processing device may be configured for analyzing the first sensor data, the second sensor data, and the third sensor data as well as rectal balloon inflation data (intrarectal balloon distension and/or pressure measurements) and a rectal sensory data (rectal sensory measurement data). Further, the processing device may be configured for determining at least one anorectal anatomical change associated with an anorectal region of a body of the user based on the analyzing. Further, the processing device may be configured for generating a visual representation of the anorectal region of the body of the user based on the at least one anorectal anatomical change and at least one information associated with the anorectal region of the body. Further, the at least one anorectal anatomical change corresponds to a change in the at least one characteristic of at least one of the first region, the second region, and the third region of the rectum. Further, the visual representation may include at least one interactive image. Further, the at least one interactive image may be dynamic. Further, the at least one interactive image changes based on the at least one maneuver. Further, the at least one maneuver corresponds to the at least one anorectal anatomical change.

Further, the communication device may be disposed on the anorectal probe. Further, the communication device may be communicatively coupled with the processing device. Further, the communication device may be configured for transmitting the visual representation of the at least one anorectal anatomical change associated with the anorectal region to at least one output device.

Further, at least one battery may be disposed on the anorectal probe. Further, the at least one battery may be electrically coupled with the plurality of sensors, the processing device, and the communication device. Further, the at least one battery may be configured for powering the plurality of sensors, the processing device, and the communication device.

Further, in some embodiments, the transmitting of the visual representation may include transmitting the visual representation of the at least one anorectal anatomical change associated with the anorectal region to the at least one output device over at least one of a wired communication channel and a wireless communication channel. Further, the wireless communication channel may include Bluetooth, ZigBee, Wi-Fi, etc.

Further, in some embodiments, the processing device may be configured for determining a state of an anorectal disorder associated with the anorectal region based on the analyzing of the first sensor data, the second sensor data, and the third sensor data. Further, the processing device may be configured for generating at least one instruction for performing at least one biofeedback maneuver based on the determining. Further, the communication device may be configured for transmitting the at least one instruction to the at least one output device. Further, the at least one instruction may include voice-guided instruction.

Further, in an embodiment, the processing device may be configured for generating a current status report corresponding to the state of the anorectal disorder for the user based on the determining of the state of the anorectal disorder. Further, the processing device may be communicatively coupled with a storage device. Further, the storage device may be configured for storing the current status report.

Further, in an embodiment, the storage device may be configured for retrieving a historical status report corresponding to a historical state of the anorectal disorder associated with the rectum of the user. Further, the processing device may be configured for analyzing the historical status report. Further, the determining of the state of the anorectal disorder may be based on the analyzing of the historical data.

FIG. 1 is a front view of a device 100 for facilitating treatment for anorectal and pelvic floor disorders of users using biofeedback therapy, in accordance with some embodiments. Accordingly, the device 100 may include a body 102 extending between a top end 104 and a bottom end 106. Further, the body 102 may be made up of silicon plastic. Further, the body 102 may include at least one core and at least one shell. Further, the at least one core may be semi flexible. Further, the at least one shell may be flexible. Further, the anorectal and pelvic floor disorders may include Dyssynergic defecation (DD), fecal incontinence (FI), and urinary incontinence (UI). Further, the body 102 may include a top end portion 108, a middle portion 110, and a bottom end portion 112. Further, the body 102 may be configured to be placed in a rectum of a user by inserting the body 102 into the rectum. Further, the top end portion 108 may be positioned adjacent to a first region of the rectum, the middle portion 110 may be positioned adjacent to a second region of the rectum, and the bottom end portion 112 may be positioned adjacent to a third region of the rectum based on the placing of the body 102 in the rectum. Further, the first region may be a region of the rectum farthest from the anus of the user. Further, the second region may be a region of the rectum in between the first region and the third region.

Further, the third region may be a region of the rectum closest to the anus. Further, the device 100 may be a bioanatoner probe.

Further, the device 100 may include a balloon 114 mounted on the top end portion 108 of the body 102. Further, the balloon 114 may include the at least one balloon. Further, the balloon 114 may include fluid bags. Further, the balloon 114 may be an air bag.

Further, the device 100 may include a plurality of sensors 116-120 that may include at least one first sensor 116, at least one second sensor 118, and at least one third sensor 120. Further, the at least one first sensor 116 may be fluidly coupled to the balloon 114. Further, the at least one first sensor 116 may include a pressure sensor, a volume sensor, etc. Further, the at least one first sensor 116 may be configured for generating at least one final first balloon data based on detecting at least one balloon characteristic (such as pressure, volume and cross-sectional area (CSA)) associated with the balloon 114 after the placing of the body 102 in the rectum. Further, the at least one final first balloon data may include balloon distension, balloon measurement, etc. Further, the at least one balloon characteristic corresponds to at least one maneuver (such as squeezing of the sphincter, relaxing of the sphincter, squeezing of the rectal muscle, relaxing of the rectal muscle, etc.) performed by the user. Further, the at least one first sensor 116 (such as a temperature sensor, a camera, an electromyography sensor, a force sensitive resistor sensor, etc.) may be configured for generating at least one first sensor data based on detecting at least one region characteristic associated with the first region. Further, the at least one region characteristic may include temperature, rectal wall lining, muscle mass, etc. Further, the at least one second sensor 118 (such as a temperature sensor, a camera, an electromyography sensor, a force sensitive resistor sensor, etc.) may be configured for generating at least one second sensor data based on detecting the at least one region characteristic associated with the second region. Further, the at least one third sensor 120 (such as a temperature sensor, a camera, an electromyography sensor, a force sensitive resistor sensor, etc.) may be configured for generating at least one third sensor data based on detecting the at least one region characteristic associated with the third region.

Further, the device 100 may include a processing device 122 communicatively coupled with the plurality of sensors 116-120. Further, the processing device 122 may be configured for analyzing the at least one final first balloon data, the at least one first sensor data, the at least one second sensor data, and the at least one third sensor data. Further, the processing device 122 may be configured for determining at least one anorectal anatomical change associated with the rectum based on the analyzing. Further, the at least one anorectal anatomical change may include a change in the position of one or more regions of the rectum, a change in the shape of the one or more regions of the rectum, contractions in the one or more regions of the rectum, tremors the one or more regions of the rectum, a change in the temperature of the one or more regions of the rectum, a change in the pressure of the one or more regions of the rectum, etc. Further, the processing device 122 may be configured for generating at least one dynamic visual representation of a human anatomy for stimulating the at least one anorectal anatomical change during the at least one maneuver in real-time based on the at least one anorectal anatomical change and a static visual representation (such as a 2D image, a 3D image, etc.) of the human anatomy. Further, the at least one dynamic visual representation may include an animation, a video, an interactive image, etc. of the human anatomy with the rectum.

Figure 2:
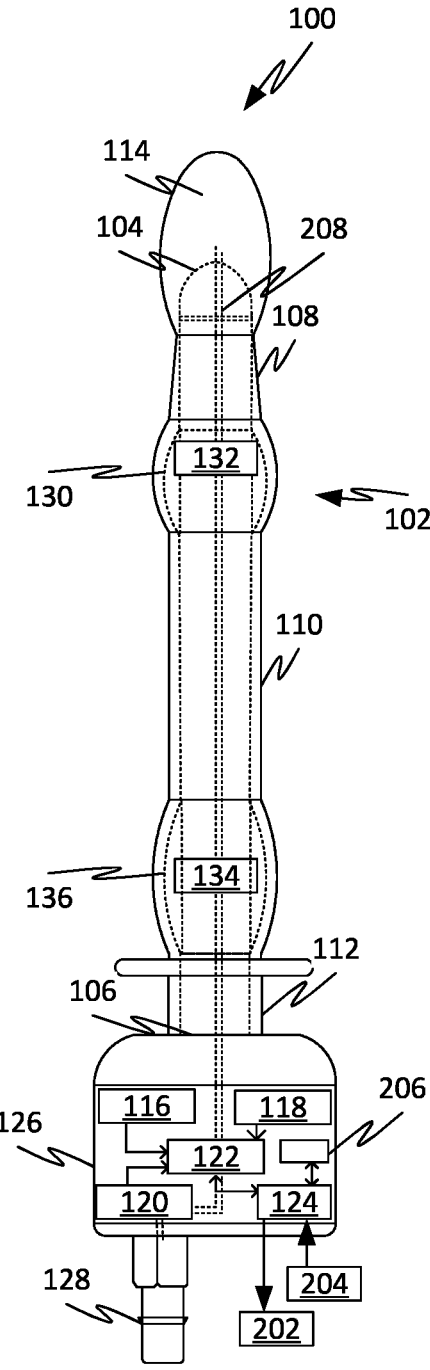
FIG. 2 is a front view of the device 100 for facilitating treatment for anorectal and pelvic floor disorders of users using biofeedback therapy, in accordance with some embodiments.

Further, the device 100 may include a communication device 124 communicatively coupled with the processing device 122. Further, the communication device 124 may be configured for transmitting the at least one dynamic visual representation to at least one output device 202 (as shown in FIG. 2). Further, the output device 202 include a display device for displaying the at least one dynamic visual representation.

In further embodiments, the device 100 may include a base 126 attached to the bottom end 106. Further, the base 126 may be not placed inside the rectum. Further, the base 126 facilitates the inserting of the body 102 in the rectum. Further, the user may insert the body 102 in the rectum by holding the base 126 and pushing the body 102 against the anus while holding the base 126.

Further, in some embodiments, the balloon 114 may be fluidly coupled with at least one port 128 comprised in the base 126 through at least one tube 208, as shown in FIG. 2. Further, the balloon 114 may be deflatably inflatable by removably transferring at least one amount of at least one fluid (such as air, water, etc.) to the balloon 114 through the at least one port 128. Further, at least one inflating device removably transfers the at least one amount of the at least one fluid (such as air, water, etc.) to the balloon 114 through the at least one port 128. Further, the at least one inflating device may include a syringe, an inflation bulb, etc. Further, the at least one inflating device may be configured to be fluidly coupled with the balloon 114 through the at least one port 128. Further, the at least one port 128 may include an opening, a conduit, an inlet, etc. Further, the at least one first sensor 116 may be configured for generating at least one initial first balloon data based on detecting the at least one balloon characteristic associated with the balloon 114 before the placing of the body 102 in the rectum. Further, the at least one initial first balloon data may include balloon distension, balloon measurement, etc. Further, the at least one balloon characteristic corresponds to the at least one amount of the at least one fluid, at least one shape of the balloon 114, etc. Further, the processing device 122 may be configured for analyzing the at least one initial first balloon data. Further, the determining of the at least one anorectal change may be based on the analyzing of the at least one initial first balloon data.

In further embodiments, the device 100 may include a second balloon 130 mounted on the middle portion 110 of the body 102. Further, the at least one second sensor 118 may be configured for detecting at least one balloon characteristic associated with the second balloon 130 after the placing of the body 102 in the rectum. Further, the processing device 122 may be configured for analyzing the at least one second balloon data. Further, the determining of the at least one anorectal change may be based on the analyzing of the at least one second balloon data. Further, in an embodiment, the second balloon 130 may be non-inflatable.

Further, in some embodiments, the second balloon 130 may be movably mounted on the middle portion 110. Further, the second balloon 130 may be configured to be moved between a plurality of positions along the middle portion 110. Further, the second balloon 130 may be configured to be slid along a length of the middle portion 110 for moving the second balloon 130 between the plurality of positions.

Further, in some embodiments, the second balloon 130 may be configured to be fastened to the middle portion 110 in one of the plurality of positions using a fastening element 132. Further, the fastening element 132 may include an adhesive element. Further, the fastening element 132 detachably fastens the second balloon 130 to the middle portion 110 in one of the plurality of positions. Further, the fastening element 132 may include magnets on in the second balloon 130 and on in the middle portion 110.

In further embodiments, the device 100 may include a third balloon 136 mounted on the bottom end portion 112 of the body 102. Further, the at least one third sensor 120 may be configured for detecting at least one balloon characteristic associated with the third balloon 136 after the placing of the body 102 in the rectum. Further, the processing device 122 may be configured for analyzing the at least one third balloon data. Further, the determining of the at least one anorectal change may be based on the analyzing of the at least one third balloon data. Further, in an embodiment, the third balloon 131 may be non-inflatable.

Further, in some embodiments, the third balloon 136 may be movably mounted on the bottom end portion 112. Further, the third balloon 136 may be configured to be moved between a plurality of positions along the bottom end portion 112. Further, the third balloon 136 may be configured to be slid along a length of the bottom end portion 112 for moving the third balloon 136 between the plurality of positions.

Further, in some embodiments, the third balloon 136 may be configured to be fastened to the bottom end portion 112 in one of the plurality of positions using a fastening element 134.

Further, in some embodiments, the communication device 124 may be configured for receiving an indication associated with the user and one of a plurality of anorectal and pelvic floor disorders from at least one input device 204 (as shown in FIG. 2). Further, the communication device 124 may be configured for transmitting at least one instruction to the at least one output device 202. Further, the device 100 may include a storage device 206 (as shown in FIG. 2) communicatively coupled with the communication device 124. Further, the storage device 206 may be configured for retrieving at least one treatment program associated with the user for one of the plurality of anorectal and pelvic floor disorders. Further, the at least one treatment program may include voice-guided instructions and written instructions displayed on the screen using the smartphone app on how to perform biofeedback training at home that mirrors the office biofeedback training. Further, the processing device 122 may be communicatively coupled with the storage device 206. Further, the processing device 122 may be configured for generating the at least one instruction for at least one therapy session based on the at least one treatment program. Further, the at least one instruction may include voice-guided instructions and written instructions. Further, the at least one instruction instructs the user for performing the at least one maneuver after the placing of the body 102 in the rectum.

Further, in some embodiments, the device 100 may include a battery electrically coupled with the at least one of the processing device 122, the storage device 206, the communication device 124, and the plurality of sensors 116-120. Further, the battery may be configured for providing electrical energy to the processing device 122, the storage device 206, the communication device 124, and the plurality of sensors 116-120.

Further, in some embodiments, the processing device 122, the storage device 206, the communication device 124, and the plurality of sensors 116-120 may be disposed in the base 126.

Further, in some embodiments, the processing device 122 may be configured for determining a state of the user with regards to one of the plurality of anorectal and pelvic floor disorders based on the analyzing of the at least one final first balloon data, the at least one first sensor data, the at least one second sensor data, and the at least one third sensor data. Further, the state of the user may include a condition of the user with respect to disease or disorder, such as recovering, stages of recovery, regressed, etc. Further, the processing device 122 may be configured for generating a current status report corresponding to the state of the user based on the determining of the state. Further, the storage device 206 may be configured for storing the current status report of the user. Further, the report may provide graphic illustrations and comparative performance charts, providing a summary of the biofeedback data analysis for at least one patient corresponding to the state of the anorectal disorder for the user.

Further, in some embodiments, the storage device 206 may be configured for retrieving a historical status report associated with a historical state of the user with regards to one of the plurality of anorectal and pelvic floor disorders based on the indication. Further, the processing device 122 may be configured for analyzing the historical status report. Further, the generating of the at least one instruction may be based on the analyzing of the historical status report.

Further, in some embodiments, the transmitting of the at least one dynamic visual representation to the at least one output device 202 may include transmitting the at least one dynamic visual representation to the at least one output device 202 over at least one wireless communication channel.

FIG. 2 is a front view of the device 100 for facilitating treatment for anorectal and pelvic floor disorders of users using biofeedback therapy, in accordance with some embodiments.

Figure 3:
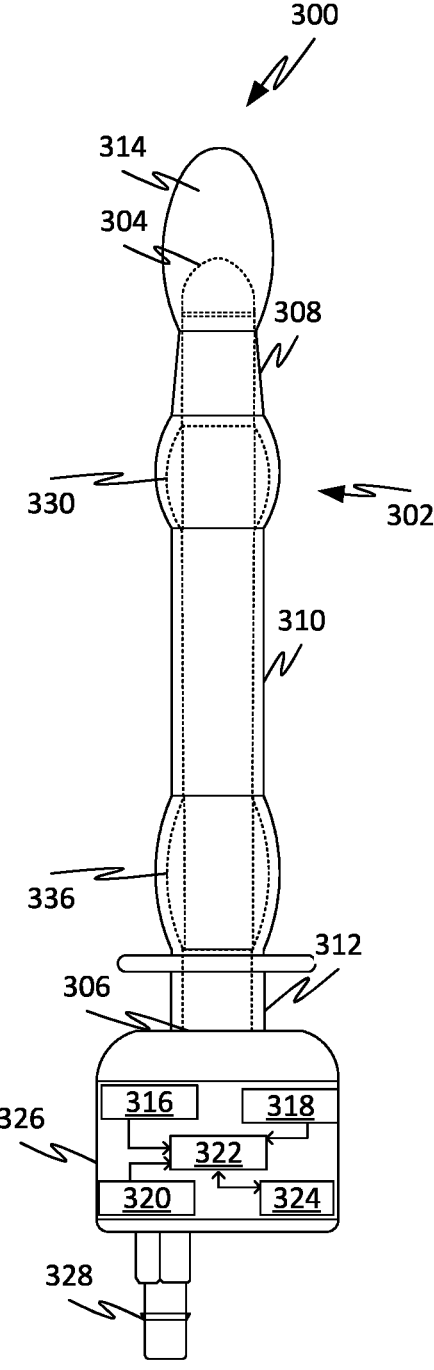
FIG. 3 is a front view of a device 300 for facilitating treatment for anorectal and pelvic floor disorders of users using biofeedback therapy, in accordance with some embodiments.

FIG. 3 is a front view of a device 300 for facilitating treatment for anorectal and pelvic floor disorders of users using biofeedback therapy, in accordance with some embodiments. Accordingly, the device 300 may include a body 302 extending between a top end 304 and a bottom end 306. Further, the body 302 may include a top end portion 308, a middle portion 310, and a bottom end portion 312. Further, the body 302 may be configured to be placed in a rectum of a user by inserting the body 302 into the rectum. Further, the top end portion 308 may be positioned adjacent to a first region of the rectum, the middle portion 310 may be positioned adjacent to a second region of the rectum, and the bottom end portion 312 may be positioned adjacent to a third region of the rectum based on the placing of the body 302 in the rectum.

Further, the device 300 may include a base 326 attached to the bottom end 306. Further, the base 326 may be not placed inside the rectum. Further, the base 326 facilitates the inserting of the body 302 in the rectum.

Further, the device 300 may include a balloon 314 mounted on the top end portion 308 of the body 302.

Further, the device 300 may include a plurality of sensors 316-320 that may include at least one first sensor 316, at least one second sensor 318, and at least one third sensor 320. Further, the at least one first sensor 316 may be configured for generating at least one final first balloon data based on detecting at least one balloon characteristic associated with the balloon 314 after the placing of the body 302 in the rectum. Further, the at least one balloon characteristic corresponds to at least one maneuver performed by the user. Further, the at least one first sensor 316 may be configured for generating at least one first sensor data based on detecting at least one region characteristic associated with the first region. Further, the at least one second sensor 318 may be configured for generating at least one second sensor data based on detecting the at least one region characteristic associated with the second region. Further, the at least one third sensor 320 may be configured for generating at least one third sensor data based on detecting the at least one region characteristic associated with the third region.

Further, the device 300 may include a processing device 322 communicatively coupled with the plurality of sensors 316-320. Further, the processing device 322 may be configured for analyzing the at least one final first balloon data, the at least one first sensor data, the at least one second sensor data, and the at least one third sensor data. Further, the processing device 322 may be configured for determining at least one anorectal anatomical change associated with the rectum based on the analyzing. Further, the processing device 322 may be configured for generating at least one dynamic visual representation of a human anatomy for stimulating the at least one anorectal anatomical change during the at least one maneuver in real-time based on the at least one anorectal anatomical change and a static visual representation of the human anatomy.

Figure 4:
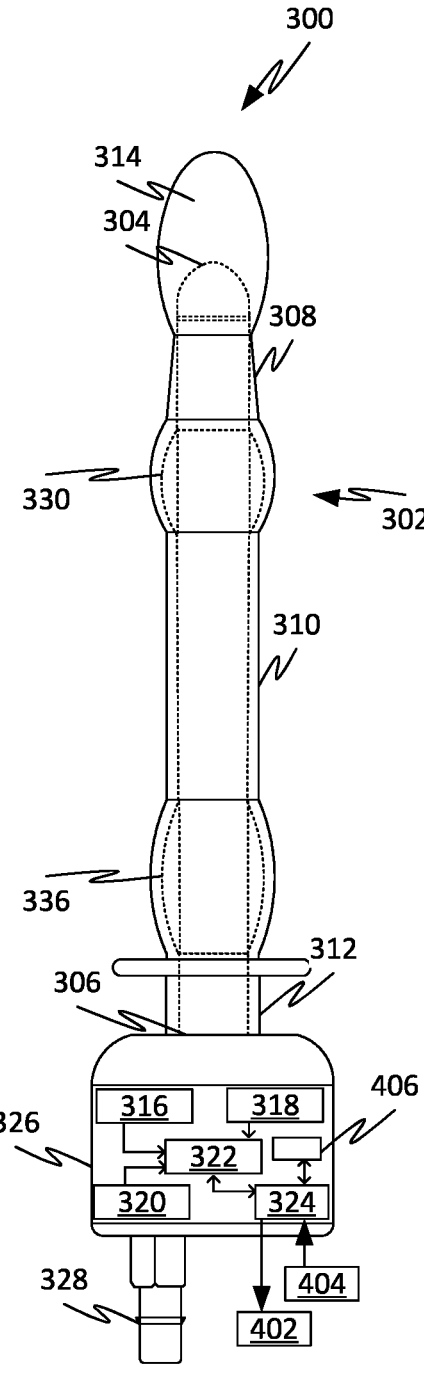
FIG. 4 is a front view of the device 300 for facilitating treatment for anorectal and pelvic floor disorders of users using biofeedback therapy, in accordance with some embodiments.

Further, the device 300 may include a communication device 324 communicatively coupled with the processing device 322. Further, the communication device 324 may be configured for transmitting the at least one dynamic visual representation to at least one output device 402 (as shown in FIG. 4).

Further, in some embodiments, the balloon 314 may be fluidly coupled with at least one port 328 comprised in the base 326 through at least one tube. Further, the balloon 314 may be deflatably inflatable by removably transferring at least one amount of at least one fluid to the balloon 314 through the at least one port 328. Further, the at least one first sensor 316 may be configured for generating at least one initial first balloon data based on detecting the at least one balloon characteristic associated with the balloon 314 before the placing of the body 302 in the rectum. Further, the at least one balloon characteristic corresponds to the at least one amount of the at least one fluid. Further, the processing device 322 may be configured for analyzing the at least one initial first balloon data. Further, the determining of the at least one anorectal change may be based on the analyzing of the at least one initial first balloon data.

In further embodiments, the device 300 may include a second balloon 330 mounted on the middle portion 310 of the body 302. Further, the at least one second sensor 318 may be configured for detecting at least one balloon characteristic associated with the second balloon 330 after the placing of the body 302 in the rectum. Further, the processing device 322 may be configured for analyzing the at least one second balloon data. Further, the determining of the at least one anorectal change may be based on the analyzing of the at least one second balloon data.

In further embodiments, the device 300 may include a third balloon 336 mounted on the bottom end portion 312 of the body 302. Further, the at least one third sensor 320 may be configured for detecting at least one balloon characteristic associated with the third balloon 336 after the placing of the body 302 in the rectum. Further, the processing device 322 may be configured for analyzing the at least one third balloon data. Further, the determining of the at least one anorectal change may be based on the analyzing of the at least one third balloon data.

Further, in some embodiments, the transmitting of the at least one dynamic visual representation to the at least one output device 402 may include transmitting the at least one dynamic visual representation to the at least one output device 402 over at least one wireless communication channel.

Further, in some embodiments, the communication device 324 may be configured for receiving an indication associated with the user and one of a plurality of anorectal and pelvic floor disorders from at least one input device 404 (as shown in FIG. 4). Further, the communication device 324 may be configured for transmitting at least one instruction to the at least one output device 402. Further, the device 300 may include a storage device 406 (as shown in FIG. 4) communicatively coupled with the communication device 324. Further, the storage device 406 may be configured for retrieving at least one treatment program associated with the user for one of the plurality of anorectal and pelvic floor disorders. Further, the processing device 322 may be communicatively coupled with the storage device 406. Further, the processing device 322 may be configured for generating the at least one instruction for at least one therapy session based on the at least one treatment program. Further, the at least one instruction instructs the user for performing the at least one maneuver after the placing of the body 302 in the rectum.

FIG. 4 is a front view of the device 300 for facilitating treatment for anorectal and pelvic floor disorders of users using biofeedback therapy, in accordance with some embodiments.

Figure 5:
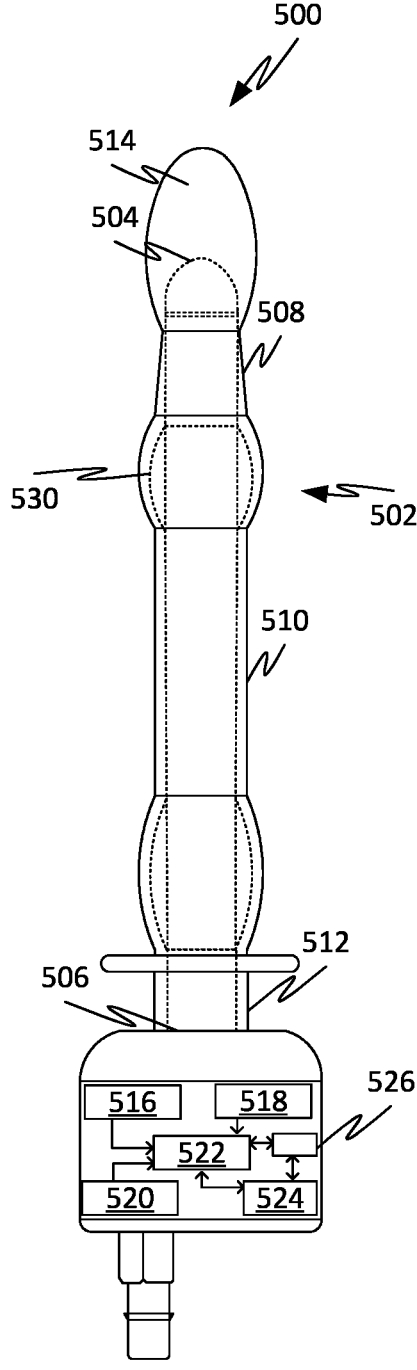
FIG. 5 is a front view of a device 500 for facilitating treatment for anorectal and pelvic floor disorders of users using biofeedback therapy, in accordance with some embodiments.

FIG. 5 is a front view of a device 500 for facilitating treatment for anorectal and pelvic floor disorders of users using biofeedback therapy, in accordance with some embodiments. Accordingly, the device 500 may include a body 502 extending between a top end 504 and a bottom end 506. Further, the body 502 may include a top end portion 508, a middle portion 510, and a bottom end portion 512. Further, the body 502 may be configured to be placed in a rectum of a user by inserting the body 502 into the rectum. Further, the top end portion 508 may be positioned adjacent to a first region of the rectum, the middle portion 510 may be positioned adjacent to a second region of the rectum, and the bottom end portion 512 may be positioned adjacent to a third region of the rectum based on the placing of the body 502 in the rectum.

Further, the device 500 may include a balloon 514 mounted on the top end portion 508 of the body 502.

Further, the device 500 may include a plurality of sensors 516-520 that may include at least one first sensor 516, at least one second sensor 518, and at least one third sensor 520. Further, the at least one first sensor 516 may be configured for generating at least one final first balloon data based on detecting at least one balloon characteristic associated with the balloon 514 after the placing of the body 502 in the rectum. Further, the at least one balloon characteristic corresponds to at least one maneuver performed by the user. Further, the at least one first sensor 516 may be configured for generating at least one first sensor data based on detecting at least one region characteristic associated with the first region. Further, the at least one second sensor 518 may be configured for generating at least one second sensor data based on detecting the at least one region characteristic associated with the second region. Further, the at least one third sensor 520 may be configured for generating at least one third sensor data based on detecting the at least one region characteristic associated with the third region.

Further, the device 500 may include a processing device 522 communicatively coupled with the plurality of sensors 516-520. Further, the processing device 522 may be configured for analyzing the at least one final first balloon data, the at least one first sensor data, the at least one second sensor data, and the at least one third sensor data. Further, the processing device 522 may be configured for determining at least one anorectal anatomical change associated with the rectum based on the analyzing. Further, the processing device 522 may be configured for generating at least one dynamic visual representation of a human anatomy for stimulating the at least one anorectal anatomical change during the at least one maneuver in real-time based on the at least one anorectal anatomical change and a static visual representation of the human anatomy.

Figure 6:
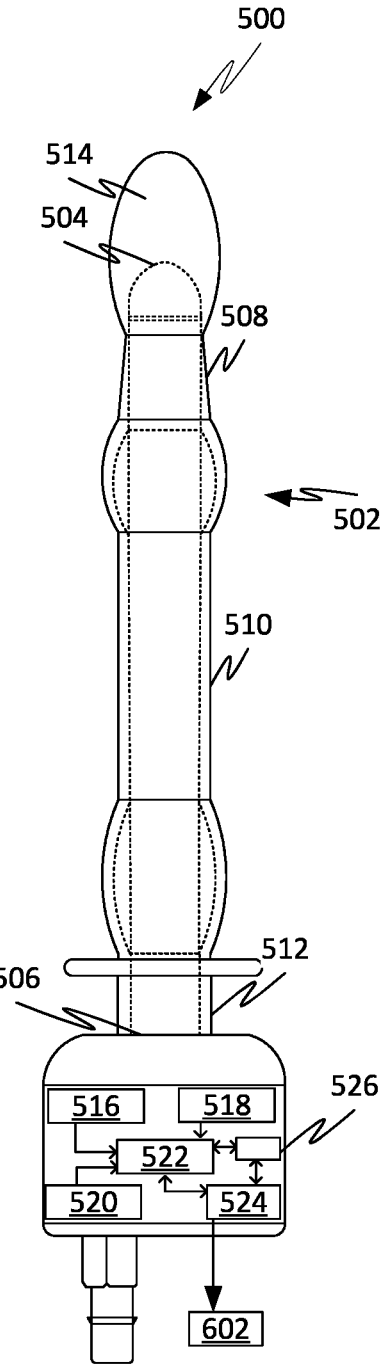
FIG. 6 is a front view of the device 500 for facilitating treatment for anorectal and pelvic floor disorders of users using biofeedback therapy, in accordance with some embodiments.

Further, the device 500 may include a communication device 524 communicatively coupled with the processing device 522. Further, the communication device 524 may be configured for transmitting the at least one dynamic visual representation to at least one output device 602 (as shown in FIG. 6). Further, the communication device 524 may be configured for receiving an indication associated with the user and one of a plurality of anorectal and pelvic floor disorders from at least one input device 604 (as shown in FIG. 6). Further, the communication device 524 may be configured for transmitting at least one instruction to the at least one output device 602.

Further, the device 500 may include a storage device 526 communicatively coupled with the communication device 524. Further, the storage device 526 may be configured for retrieving at least one treatment program associated with the user for one of the plurality of anorectal and pelvic floor disorders. Further, the processing device 522 may be communicatively coupled with the storage device 526. Further, the processing device 522 may be configured for generating the at least one instruction for at least one therapy session based on the at least one treatment program. Further, the at least one instruction instructs the user for performing the at least one maneuver after the placing of the body 502 in the rectum.

FIG. 6 is a front view of the device 500 for facilitating treatment for anorectal and pelvic floor disorders of users using biofeedback therapy, in accordance with some embodiments.

Figure 7:
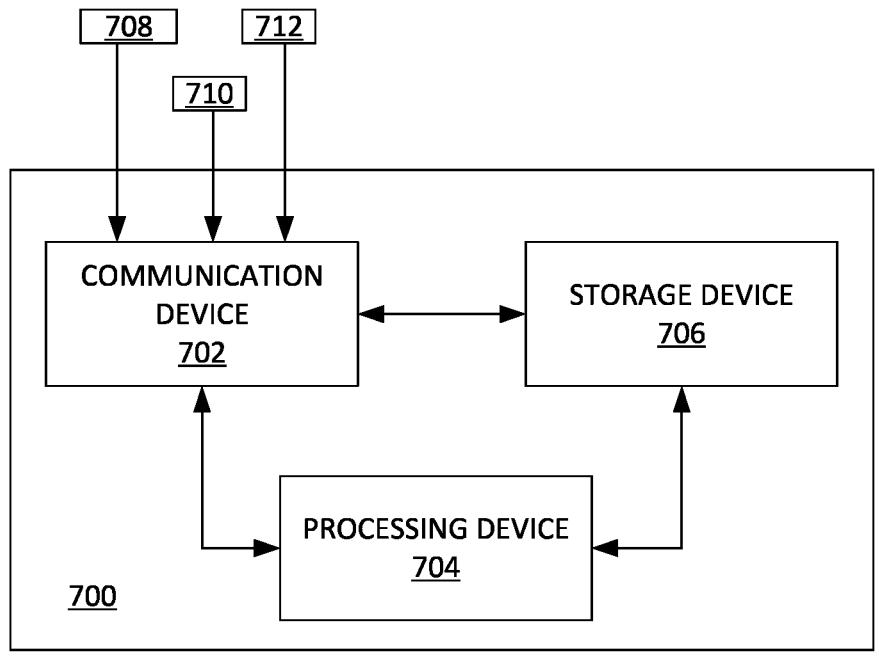
FIG. 7 is a block diagram of a system 700 for performing biofeedback treatment of anorectal and pelvic floor disorders, in accordance with some embodiments.

FIG. 7 is a block diagram of a system 700 for performing biofeedback treatment of anorectal and pelvic floor disorders, in accordance with some embodiments. Accordingly, the system 700 may include a communication device 702, a processing device 704, and a storage device 706. Further, the anorectal and pelvic floor disorders may include Dyssynergic defecation (DD), fecal incontinence (FI), and urinary incontinence (UI).

Further, the communication device 702 may be configured for receiving a plurality of sensor data from a plurality of sensors 708-712. Further, the plurality of sensors 708-712 may include a first sensor, a second sensor, and a third sensor. Further, the first sensor may be configured for generating a first sensor data based on detecting at least one characteristic associated with a first region of a rectum of a user during at least one maneuver performed by the user. Further, the second sensor may be configured for generating a second sensor data based on detecting the at least one characteristic associated with a second region of the rectum during the at least one maneuver performed by the user. Further, the third sensor may be configured for generating a third sensor data based on detecting the at least one characteristic associated with a third region of the rectum during the at least one maneuver performed by the user. Further, the at least one characteristic may include a movement, a pressure, a temperature, a void, a shape, etc. associated with at least one of the first region, the second region, and the third region of the rectum. Further, the plurality of sensor data may include the first sensor data, the second sensor data, and the third sensor data. Further, the communication device 702 may be configured for transmitting a visual representation of at least one anorectal anatomical change associated with an anorectal region to at least one output device.

Further, the processing device 704 may be communicatively coupled with the communication device 702. Further, the processing device 704 may be configured for analyzing the plurality of sensor data. Further, the processing device 704 may be configured for determining the at least one anorectal anatomical change associated with an anorectal region of a body of the user based on the analyzing. Further, the processing device 704 may be configured for generating a visual representation of the anorectal region of the body of the user based on the at least one anorectal anatomical change and at least one information associated with the anorectal region of the body. Further, the at least one anorectal anatomical change corresponds to a change in the at least one characteristic of at least one of the first region, the second region, and the third region of the rectum. Further, the visual representation may include at least one interactive image. Further, the at least one interactive image may be dynamic. Further, the at least one interactive image changes based on the at least one maneuver. Further, the at least one maneuver corresponds to the at least one anorectal anatomical change.

Further, the storage device 706 may be communicatively coupled with the processing device 704. Further, the storage device 706 may be configured for storing the visual representation.

FIG. 8 is a flowchart of a method 800 for performing biofeedback treatment of anorectal and pelvic floor disorders, in accordance with some embodiments. Accordingly, at 802, the method 800 may include receiving, using a communication device, a plurality of sensor data from a plurality of sensors. Further, the plurality of sensors may include a first sensor, a second sensor, and a third sensor. Further, the first sensor may be configured for generating a first sensor data based on detecting at least one characteristic associated with a first region of a rectum of a user during at least one maneuver performed by the user. Further, the second sensor may be configured for generating a second sensor data based on detecting the at least one characteristic associated with a second region of the rectum during the at least one maneuver performed by the user. Further, the third sensor may be configured for generating a third sensor data based on detecting the at least one characteristic associated with a third region of the rectum during the at least one maneuver performed by the user. Further, the plurality of sensor data may include the first sensor data, the second sensor data, and the third sensor data. Further, the at least one characteristic may include a movement, a pressure, a temperature, a void, a shape, etc. associated with at least one of the first region, the second region, and the third region of the rectum.

Further, at 804, the method 800 may include analyzing, using a processing device, the plurality of sensor data.

Further, at 806, the method 800 may include determining, using the processing device, at least one anorectal anatomical and/or pressure change associated with an anorectal region of a body of the user based on the analyzing. Further, the analyzing may include an analysis of measurements inside the rectum.

Further, at 808, the method 800 may include generating, using the processing device, a visual representation of the anorectal region of the body of the user based on the at least one anorectal anatomical change and at least one information associated with the anorectal region of the body. Further, the at least one anorectal anatomical change corresponds to a change in the at least one characteristic of at least one of the first region, the second region, and the third region of the rectum.

Further, at 810, the method 800 may include transmitting, using the communication device, the visual representation of the at least one anorectal anatomical change associated with the anorectal region to at least one output device.

Further, at 812, the method 800 may include storing, using a storage device, the visual representation of the pressure or anatomical configurations as generated during dynamic changes that occur in the body when performing various maneuvers typically used during biofeedback treatment. Further, the visual representation may include real-time dynamic simulations of the anorectal configurations and/or the presence of a simulated stool. Further, the communication device may include voice-guided audio instructions as well as visual instructions on how to perform biofeedback treatment using a standardized stepwise protocol for dyssynergic defecation, FI, and UI.

Figure 9:
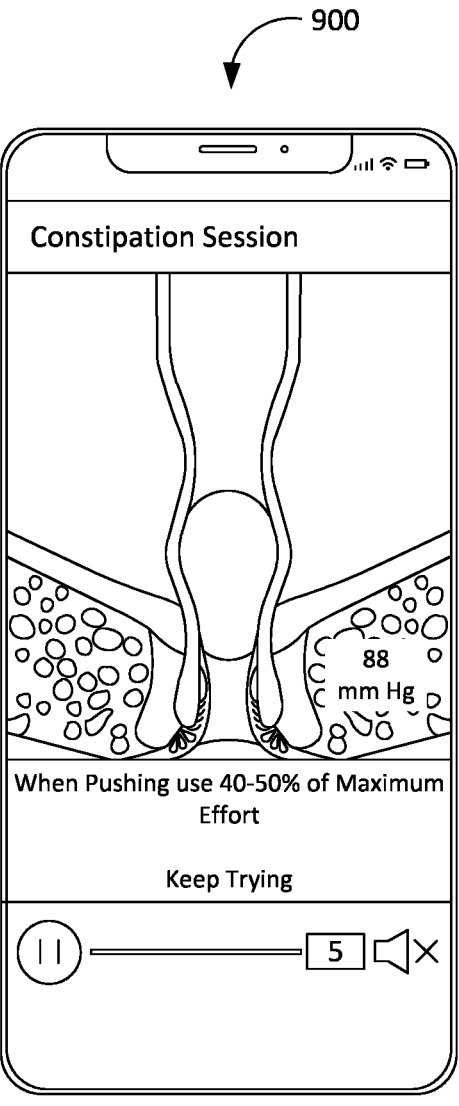
FIG. 9 illustrates a visual representation 900 of the anorectal region of the body, in accordance with some embodiments.

FIG. 9 illustrates a visual representation 900 of the anorectal region of a body of the user, in accordance with some embodiments.

Figure 10:
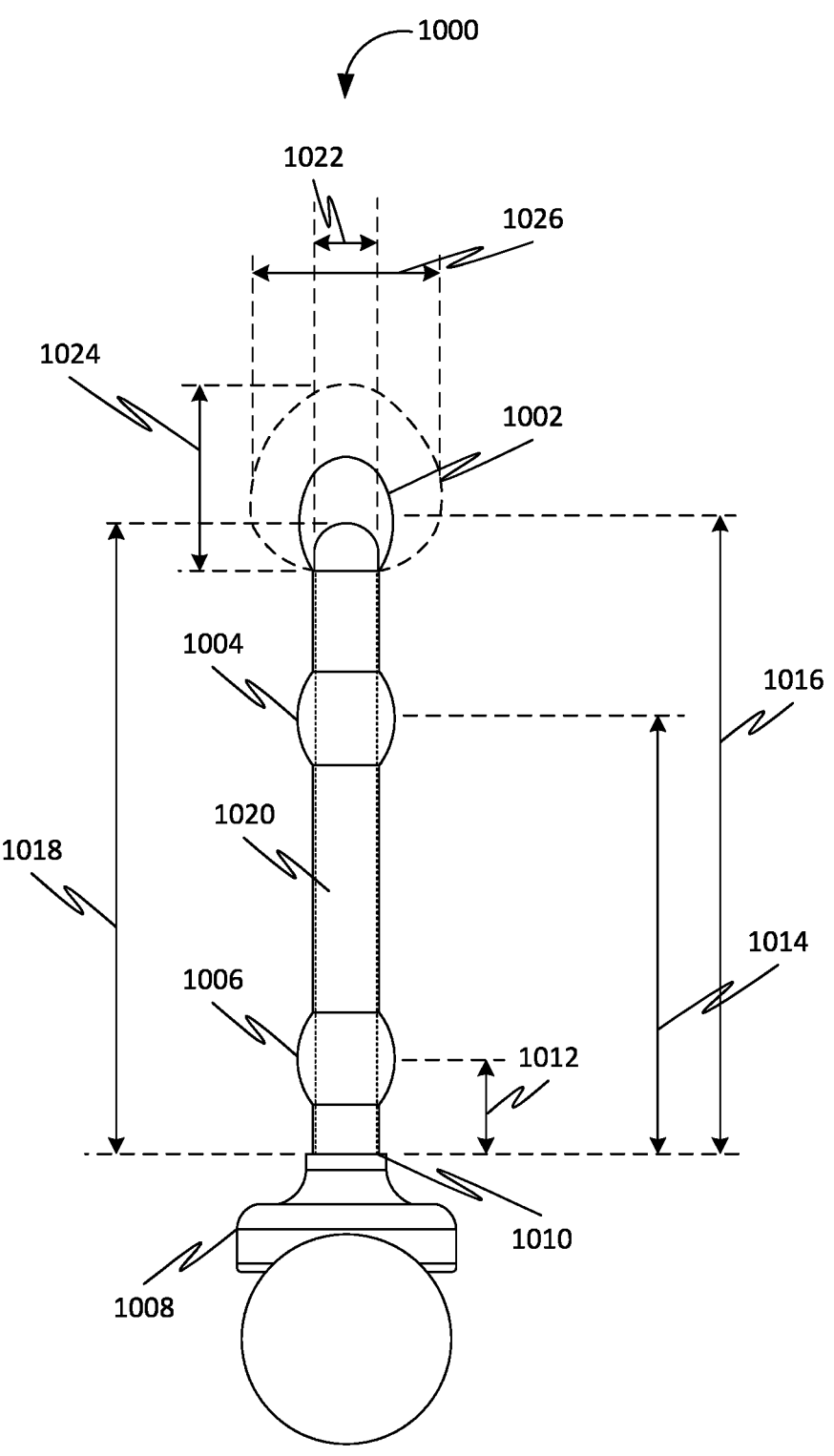
FIG. 10 is a front view of an apparatus 1000 for performing biofeedback treatment of anorectal and pelvic floor disorders, in accordance with some embodiments.

FIG. 10 is a front view of an apparatus 1000 for performing biofeedback treatment of anorectal and pelvic floor disorders, in accordance with some embodiments. Accordingly, the apparatus 1000 may include a balloon 1002 (the balloon 114), a rectal balloon 1004 (the second balloon 130), and an anal balloon 1006 (the third balloon 136). Further, a distance 1012 between a midpoint of the anal balloon 1006 and a proximal end 1010 of a base 1008 of the apparatus 1000 may be 18 mm or 0.71 inches. Further, a distance 1014 between a midpoint of the rectal balloon 1004 and the proximal end 1010 of the base 1008 of the apparatus 1000 may be 82 mm or 3.23 inches. Further, a distance 1016 between a midpoint of the balloon 1002 and the proximal end 1010 of the base 1008 may be 120 mm or 4.73 inches. Further, a length 1018 of a core 1020 of the apparatus 1000 may be 118.5 mm or 4.67 inches and a diameter 1022 of the core 1020 may be 12 mm or 0.47 inches. Further, a length 1024 of the balloon 1002 may be 35 mm or 1.38 inches and a width 1026 of the balloon 1002 may be 35 mm or 1.38 inches in an inflated state.

Figure 11:
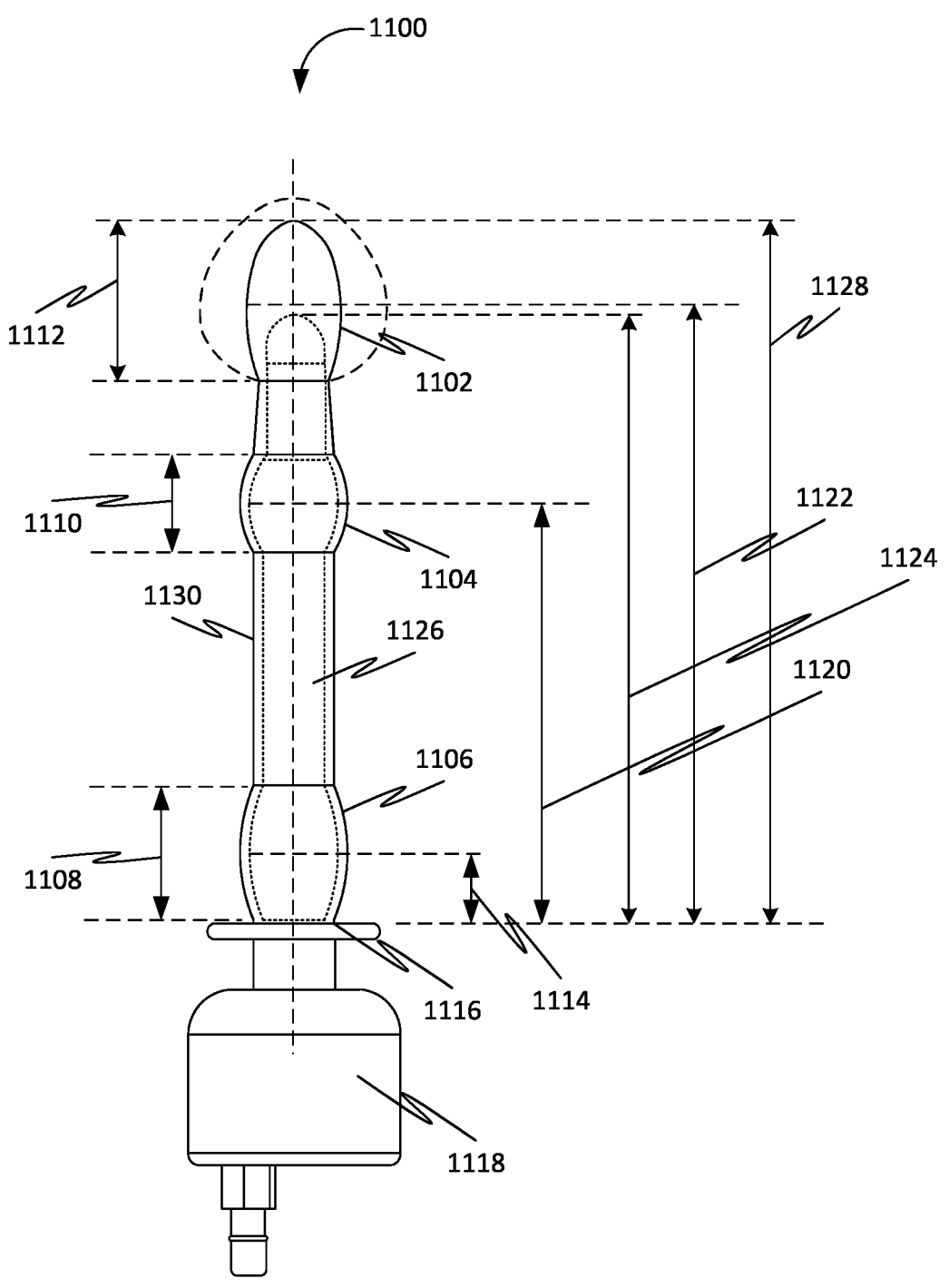
FIG. 11 is a front view of an apparatus 1100 for performing biofeedback treatment of anorectal and pelvic floor disorders, in accordance with some embodiments.

FIG. 11 is a front view of an apparatus 1100 for performing biofeedback treatment of anorectal and pelvic floor disorders, in accordance with some embodiments. Accordingly, the apparatus 1100 may include a balloon 1102 (the balloon 114), a rectal balloon 1104 (the second balloon 130), and an anal balloon 1106 (the third balloon 136). Further, a length 1108 of the anal balloon 1106 may be 25.8 mm or 1.02 inches, a length 1110 of the rectal balloon 1104 may be 18.7 mm or 0.74 inches, and a length 1112 of the balloon 1102 may be 31 mm or 1.22 inches. Further, a distance 1114 between a midpoint of the anal balloon 1108 and a proximal end 1116 of a base 1118 of the apparatus 1100 may be 13.7 mm or 0.54 inches. Further, a distance 1120 between a midpoint of the rectal balloon 1104 and the proximal end 1116 of the base 1118 of the apparatus 1100 may be 81.1 mm or 3.19 inches. Further, a distance 1122 between a midpoint of the balloon 1102 and the proximal end 1116 of the base 1118 may be 119.7 mm or 4.71 inches. Further, a length 1124 of a core 1126 of the apparatus 1100 may be 117.5 mm or 4.62 inches. Further, a length 1128 of a body 1130 of the apparatus 1100 may be 135.9 mm or 5.35 inches.

Figure 12:
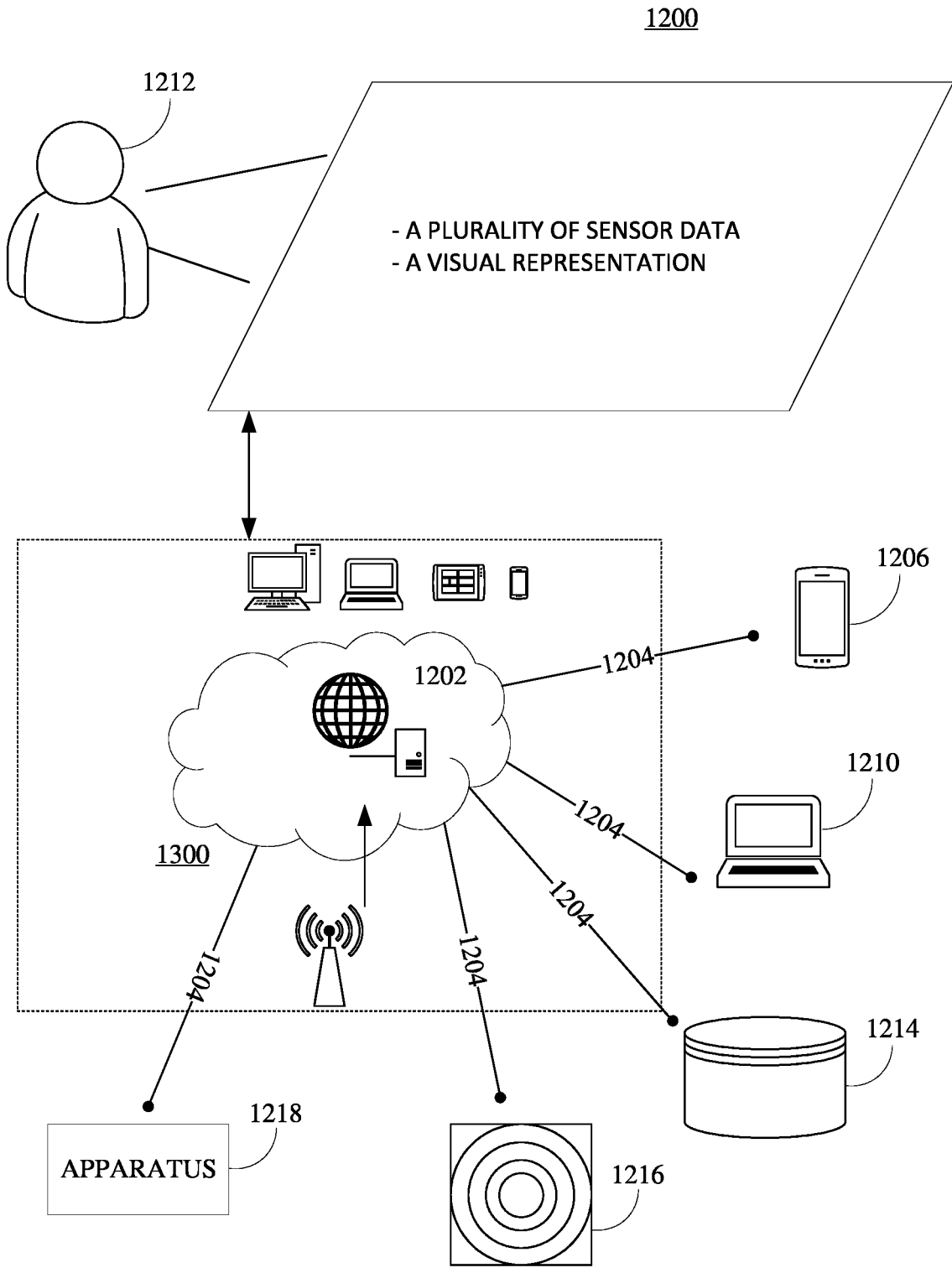
FIG. 12 is an illustration of an online platform consistent with various embodiments of the present disclosure.

FIG. 12 is an illustration of an online platform 1200 consistent with various embodiments of the present disclosure. By way of non-limiting example, the online platform 1200 for facilitating treatment for anorectal and pelvic floor disorders of users using biofeedback therapy may be hosted on a centralized server 1202, such as, for example, a cloud computing service. The centralized server 1202 may communicate with other network entities, such as, for example, a mobile device 1206 (such as a smartphone, a laptop, a tablet computer, etc.), other electronic devices 1210 (such as desktop computers, server computers, etc.), databases 1214, sensors 1216, and an apparatus 1218 (such as the device 100 for facilitating treatment for anorectal and pelvic floor disorders of users using biofeedback therapy) over a communication network 1204, such as, but not limited to, the Internet. Further, users of the online platform 1200 may include relevant parties such as, but not limited to, end-users, administrators, service providers, service consumers and so on. Accordingly, in some instances, electronic devices operated by the one or more relevant parties may be in communication with the platform.

A user 1212, such as the one or more relevant parties, may access online platform 1200 through a web-based software application or browser. The web-based software application may be embodied as, for example, but not be limited to, a website, a web application, a desktop application, and a mobile application compatible with a computing device 1300.

Figure 13:
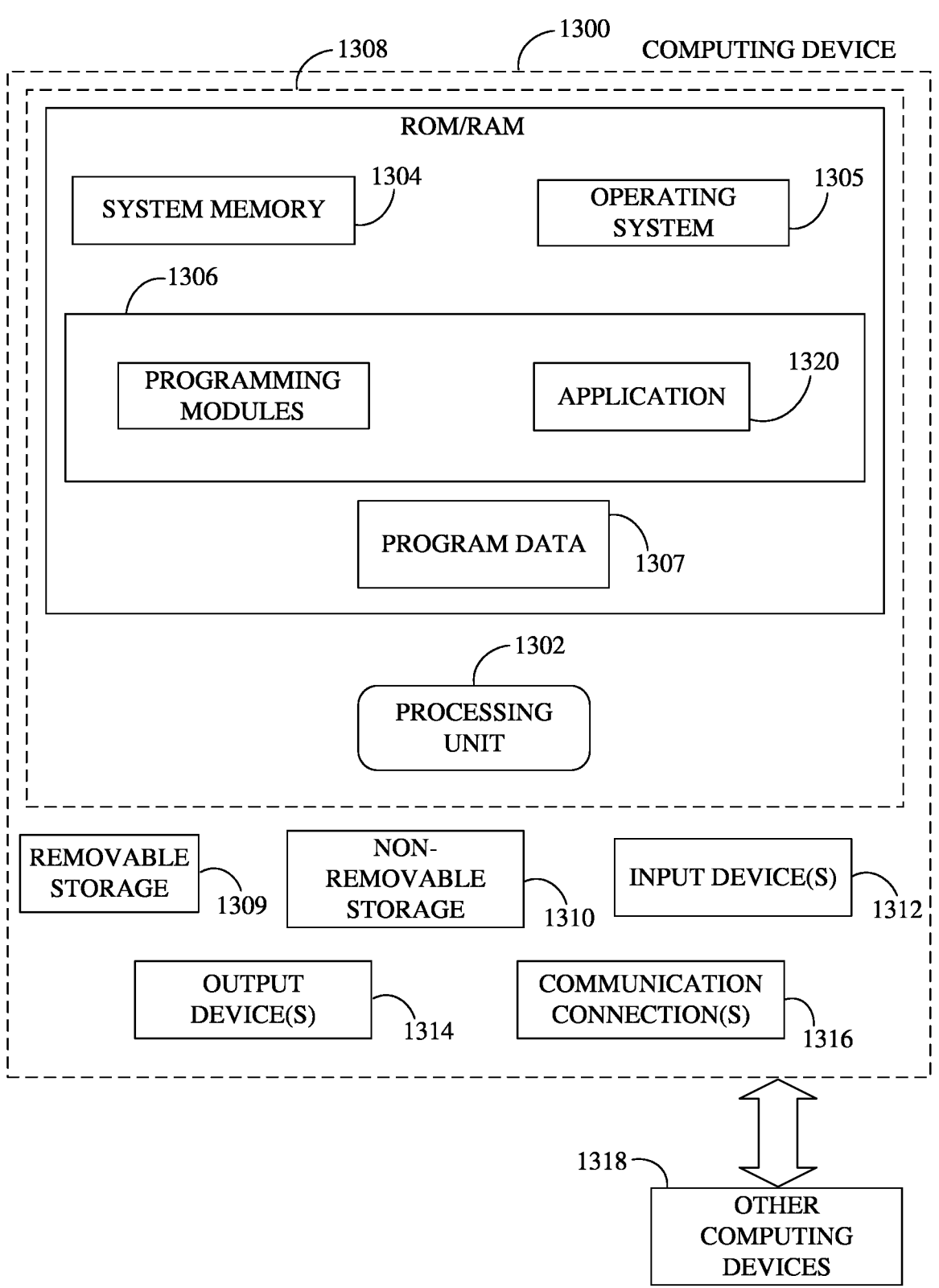
FIG. 13 is a block diagram of a computing device for implementing the methods disclosed herein, in accordance with some embodiments.

With reference to FIG. 13, a system consistent with an embodiment of the disclosure may include a computing device or cloud service, such as computing device 1300. In a basic configuration, computing device 1300 may include at least one processing unit 1302 and a system memory 1304. Depending on the configuration and type of computing device, system memory 1304 may comprise, but is not limited to, volatile (e.g., random-access memory (RAM)), non-volatile (e.g., read-only memory (ROM)), flash memory, or any combination. System memory 1304 may include operating system 1305, one or more programming modules 1306, and may include a program data 1307. Operating system 1305, for example, may be suitable for controlling computing device 1300's operation. In one embodiment, programming modules 1306 may include image-processing module, machine learning module. Furthermore, embodiments of the disclosure may be practiced in conjunction with a graphics library, other operating systems, or any other application program and is not limited to any particular application or system. This basic configuration is illustrated in FIG. 13 by those components within a dashed line 1308.

Computing device 1300 may have additional features or functionality. For example, computing device 1300 may also include additional data storage devices (removable and/or non-removable) such as, for example, magnetic disks, optical disks, or tape. Such additional storage is illustrated in FIG. 13 by a removable storage 1309 and a non-removable storage 1310. Computer storage media may include volatile and non-volatile, removable and non-removable media implemented in any method or technology for storage of information, such as computer-readable instructions, data structures, program modules, or other data. System memory 1304, removable storage 1309, and non-removable storage 1310 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 1300. Any such computer storage media may be part of device 1300. Computing device 1300 may also have input device(s) 1312 such as a keyboard, a mouse, a pen, a sound input device, a touch input device, a location sensor, a camera, a biometric sensor, etc. Output device(s) 1314 such as a display, speakers, a printer, etc. may also be included. The aforementioned devices are examples and others may be used.

Computing device 1300 may also contain a communication connection 1316 that may allow device 1300 to communicate with other computing devices 1318, such as over a network in a distributed computing environment, for example, an intranet or the Internet. Communication connection 1316 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 1304, including operating system 1305. While executing on processing unit 1302, programming modules 1306 (e.g., application 1320) may perform processes including, for example, one or more stages of methods, algorithms, systems, applications, servers, databases as described above. The aforementioned process is an example, and processing unit 1302 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

REFERENCES

1. Rao S S, Rattanakovit K, Patcharatrakul T. Diagnosis and management of chronic constipation in adults. Nat Rev Gastroenterol Hepatol 2016; 13:295-305.
2. Menees S B, Almario C V, Spiegel B M R, et al. Prevalence of and Factors Associated With Fecal Incontinence: Results From a Population-Based Survey. Gastroenterology 2018; 154:1672-1681 e.
3. Aoki, Y., Brown, H. W., Brubaker, L., Cornu, J. N., Daly, J. O., & Cartwright, R. Urinary incontinence in women. *Nature reviews. Disease primers* 2017; 3, 17042. https://doi.org/10.1038/nrdp.2017.42
4. Rao S, Camilleri M. 'Clinical approach to constipation'. In Yamada's Text Book of Gastroenterology, Edited by Podolsky D et al., Chapter 42. (2016): 757-780.
5. Curtin B, Jimenez E, Rao S S C. Clinical Evaluation of a Patient With Symptoms of Colonic or Anorectal Motility Disorders. J Neurogastroenterol Motil 2020; 26:423-436.
6. Rao S S, Benninga M A, Bharucha A E, et al. ANMS-ESNM position paper and consensus guidelines on biofeedback therapy for anorectal disorders. Neurogastroenterol Motil 2015; 27:594-609.
7. Rao S S C, Valestin J A, Xiang X, et al. Home-based versus office-based biofeedback therapy for constipation with dyssynergic defecation: a randomised controlled trial. Lancet Gastroenterol Hepatol 2018; 3:768-777.
8. Rao S S, Seaton K, Miller M, et al. Randomized controlled trial of biofeedback, sham feedback, and standard therapy for dyssynergic defecation. Clin Gastroenterol Hepatol 2007; 5:331-8.
9. Firinci S, Yildiz N, Alkan H, Aybek Z. Which combination is most effective in women with idiopathic overactive bladder, including bladder training, biofeedback, and electrical stimulation? A prospective randomized controlled trial. Neurourol Urodyn. 2020; 39(8):2498-508.
10. Rao S S C, Go J T, Valestin J, et al. Home Biofeedback for the Treatment of Dyssynergic Defecation: Does It Improve Quality of Life and Is It Cost-Effective? Am J Gastroenterol 2019; 114:938-944.
11. Rao S S, Bharucha A E, Chiarioni G, et al. Anorectal Disorders. Gastroenterology 2016; 150:1430-1442.
12. Jiang A C, Panara A, Yan Y, et al. Assessing Anorectal Function in Constipation and Fecal Incontinence. Gastroenterol Clin North Am 2020; 49:589-606. Yan Y, Xiang X, Sharma A, et al. Validation of a prospective stool diary instrument for assessment of fecal incontinence. Gastroenterology 2019; 156:S-355.
13. Rao S S, Coss-Adame E, Tantiphlachiva K, et al. Translumbar and transsacral magnetic neurostimulation for the assessment of neuropathy in fecal incontinence. Dis Colon Rectum 2014; 57:645-52.
14. Yan Y, Jimenez E, Sharma A, et al. How useful is constipation stool app compared to paper stool dairy-randomized study of constipation and healthy subjects. Gastroenterology 2020; 158:S400.
15. Jimenez E, Yan Y, Sharma A, Parr R, Herekar A, Eubanks A, Karunaratne T, Sanku A, Rao S S C. Fecal Incontinence (FI) Stool APP is a Reliable and Valid Instrument for Leakage Assessment: RCT in FI and Healthy Subjects. J Gastroenterol & Hepatol 2019; 34:457-457. Sa1681.

16. Rao S S. Endpoints for therapeutic interventions in fecal incontinence: small step or game changer. Neurogastroenterol Motil 2016; 28:1123-33.

17. Patcharatrakul T, Pitisuttithum P, Rao S, et al. 'Biofeedback therapy'. In: Rao S S, Lee Y Y, Ghoshal U C, ed. Clinical and basic neurogastroenterology and motility. 1st Ed. Cambridge, MA, USA, Academic Press 2020; 517-532.

18. Whitehead W, Rao S S C, Lowry A, Nagle D, Varma M, Bitar K, Bharucha A, Hamilton F. Treatment of Fecal Incontinence: State-of-the-Science Summary for the National Institute of Diabetes and Digestive and Kidney Disease Workshop. Am J Gastroenterol. 2015; 110(1): 138-46. Epub 2014 Oct. 21. PMID: 25331348.

19. Haddix A C, Teutsch S M, Corso P S, editors. Prevention effectiveness: a guide to decision analysis and economic evaluation. Oxford University Press; 2003.

20. Xiang X, Sharma A, Patcharatrakul T, Yan Y, Karunaratne T, Parr R, Ayyala D N, Hall P, Rao S S. Randomized controlled trial of home biofeedback therapy versus office biofeedback therapy for fecal incontinence. Neurogastroenterology & Motility. 2021 November; 33(11):e14168.

What is claimed is:

1. A device for facilitating treatment for anorectal and pelvic floor disorders of users using biofeedback therapy, the device comprising:

a body extending between a top end and a bottom end, wherein the body comprises a top end portion, a middle portion, and a bottom end portion, wherein the body is configured to be placed in a rectum of a user by inserting the body into the rectum, wherein the top end portion is positioned adjacent to a first region of the rectum, the middle portion is positioned adjacent to a second region of the rectum, and the bottom end portion is positioned adjacent to a third region of the rectum based on the placing of the body in the rectum;

a base attached to the bottom end, wherein the base is not placed inside the rectum, wherein the base facilitates the inserting of the body in the rectum;

a balloon mounted on the top end portion of the body;

a plurality of sensors comprising at least one first sensor, at least one second sensor, and at least one third sensor, wherein the at least one first sensor is configured for:

generating at least one final first balloon data based on detecting at least one balloon characteristic associated with the balloon after the placing of the body in the rectum, wherein the at least one balloon characteristic corresponds to at least one voluntary maneuver performed by the user; and generating at least one first sensor data based on detecting at least one region characteristic associated with the first region, wherein the at least one second sensor is configured for generating at least one second sensor data based on detecting the at least one region characteristic associated with the second region, wherein the at least one third sensor is configured for generating at least one third sensor data based on detecting the at least one region characteristic associated with the third region;

a processing device communicatively coupled with the plurality of sensors, wherein the processing device is configured for:

analyzing the at least one final first balloon data, the at least one first sensor data, the at least one second sensor data, and the at least one third sensor data;

determining at least one anorectal anatomical change associated with the rectum based on the analyzing; and generating at least one dynamic visual representation of a human anatomy for stimulating the at least one anorectal anatomical change during the at least one voluntary maneuver in real-time based on the at least one anorectal anatomical change and a static visual representation of the human anatomy;

a communication device communicatively coupled with the processing device, wherein the communication device is configured for wirelessly transmitting the at least one dynamic visual representation to at least one output device;

a second balloon mounted on the middle portion of the body, wherein the at least one second sensor is further configured for detecting at least one balloon characteristic associated with the second balloon after the placing of the body in the rectum, wherein the processing device is further configured for analyzing the at least one second balloon data, wherein the determining of the at least one anorectal change is further based on the analyzing of the at least one second balloon data, wherein the second balloon is movably mounted on the middle portion, wherein the second balloon is configured to be moved between a plurality of positions along the middle portion; and a third balloon mounted on the bottom end portion of the body, wherein the at least one third sensor is further configured for detecting at least one balloon characteristic associated with the third balloon after the placing of the body in the rectum, wherein the processing device is further configured for analyzing the at least one third balloon data, wherein the determining of the at least one anorectal change is further based on the analyzing of the at least one third balloon data.

2. The device of claim 1, wherein the balloon is fluidly coupled with at least one port comprised in the base through at least one tube, wherein the balloon deflatably inflatable by removably transferring at least one amount of at least one fluid to the balloon through the at least one port, wherein the at least one first sensor is further configured for generating at least one initial first balloon data based on detecting the at least one balloon characteristic associated with the balloon before the placing of the body in the rectum, wherein the at least one balloon characteristic corresponds to the at least one amount of the at least one fluid, wherein the processing device is further configured for analyzing the at least one initial first balloon data, wherein the determining of the at least one anorectal change is further based on the analyzing of the at least one initial first balloon data.

3. The device of claim 1, wherein the second balloon is further configured to be fastened to the middle portion in one of the plurality of positions using a fastening element.

4. The device of claim 1, wherein the third balloon is movably mounted on the bottom end portion, wherein the third balloon is configured to be moved between a plurality of positions along the bottom end portion.

5. The device of claim 4, wherein the third balloon is further configured to be fastened to the bottom end portion in one of the plurality of positions using a fastening element.

6. The device of claim 1, wherein the communication device is configured for:

receiving an indication associated with the user and one of a plurality of anorectal and pelvic floor disorders from at least one input device; and transmitting at least one instruction to the at least one output device, wherein the device comprises a storage device communicatively coupled with the communication device, wherein the storage device is further configured for retrieving at least one treatment program associated with the user for one of the plurality of anorectal and pelvic floor disorders, wherein the processing device is communicatively coupled with the storage device, wherein the processing device is further configured for generating the at least one instruction for at least one therapy session based on the at least one treatment program, wherein the at least one instruction instructs the user for performing the at least one voluntary maneuver after the placing of the body in the rectum.

7. The device of claim 6, wherein the processing device is further configured for:

determining a state of the user with regards to one of the plurality of anorectal and pelvic floor disorders based on the analyzing of the at least one final first balloon data, the at least one first sensor data, the at least one second sensor data, and the at least one third sensor data; and generating a current status report corresponding to the state of the user based on the determining of the state, wherein the storage device is further configured for storing the current status report of the user.

8. The device of claim 6, wherein the storage device is further configured for retrieving a historical status report associated with a historical state of the user with regards to one of the plurality of anorectal and pelvic floor disorders based on the indication, wherein the processing device is further configured for analyzing the historical status report, wherein the generating of the at least one instruction is further based on the analyzing of the historical status report.

9. The device of claim 1, wherein the transmitting of the at least one dynamic visual representation to the at least one output device comprises transmitting the at least one dynamic visual representation to the at least one output device over at least one wireless communication channel.

* * * * *